United States Patent [19]

Libke et al.

[11] Patent Number: 5,449,000
[45] Date of Patent: Sep. 12, 1995

[54] SYSTEM FOR BODY IMPEDANCE DATA ACQUISITION UTILIZING SEGMENTAL IMPEDANCE & MULTIPLE FREQUENCY IMPEDANCE

[75] Inventors: Albert W. Libke; Richard Wooten, both of Beaverton, Oreg.

[73] Assignee: ABC Development, Beaverton, Oreg.

[21] Appl. No.: 76,554

[22] Filed: Jun. 11, 1993

Related U.S. Application Data

[63] Continuation-in-part of Ser. No. 197,995, May 24, 1988, Pat. No. 4,895,163.

[51] Int. Cl.$^6$ ............................................. A61B 5/05
[52] U.S. Cl. .................................................. 128/734
[58] Field of Search ............................... 128/734, 639

[56] References Cited

U.S. PATENT DOCUMENTS 4,895,163  1/1990  Libke et al. .................... 128/734
4,911,175  3/1990  Shizgal ............................ 128/734

Primary Examiner—William E. Kamm
Assistant Examiner—Scott M. Getzow
Attorney, Agent, or Firm—Frank Frisenda, Jr.

[57] ABSTRACT

The unique system of the present invention provides an accurate valid measurement of human body composition consisting of fat tissue, lean tissue and body water. The inventive methodology provides a procedure for quantitative measurement of the conductive potential of the body, which is based on the lean tissue content of the body, in a convenient and reliable manner. In more detail, the quantitative measurement in accordance with the present invention is referred to as a "bio-impedance signal." This electrical signal, in ohms, is derived from a means for measuring body impedance component of the system. The resultant signal (three digit number, between 1 and 1000 ohms) is then entered into a modifying means component to accurately predict the body composition of the tested individual. The unique modifying component, in one embodied form, comprises prediction formulas derived from biological data inputs including: a patient's height, weight, age, and sex to determine a "population prediction variable." Thus, the unique modifying component of the inventive system interprets bio-impedance readings as "population specific", i.e., specific impedance values are exhibited by various pre-defined populations of individuals. This specificity is related to morph-type, leanness, body water and age.

9 Claims, 28 Drawing Sheets

BLOCK DIAGRAM

FIG. 9

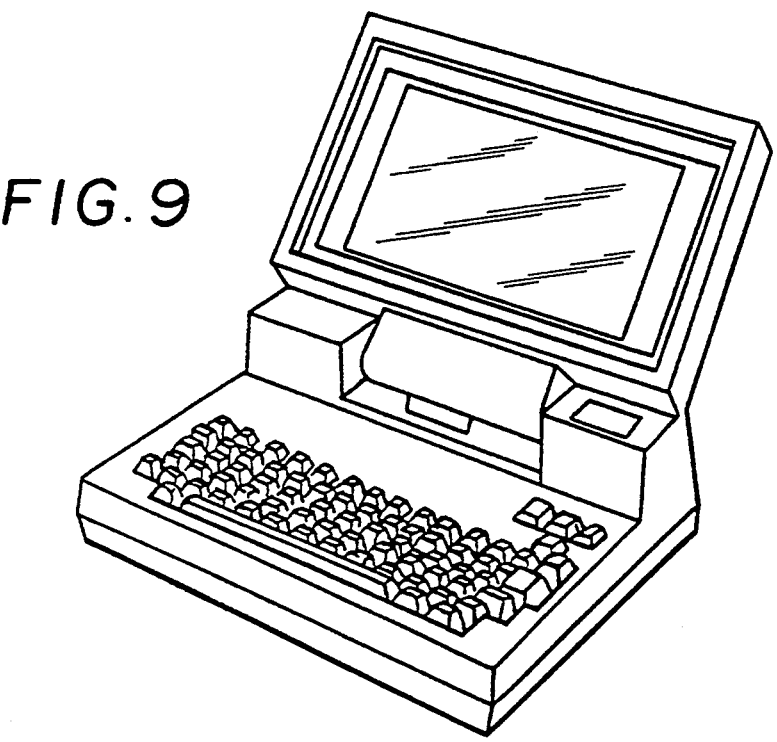

FIG. II

INTER-METRE COMPARISONS

THE FOLLOWING SPREAD DATA SHEETS ARE THE RESULT OF AN "IN-HOUSE" STUDY TO DEMONSTRATE THE TEST RE-TEST RELIABILITY OF THE BID-OHM METRE PRODUCED BY BODY COMPOSITION ANALOG, INC. THE TESTING WAS DONE AT THE BEAVERTON, ORE. FACILITY.

SUBJECT GROUP A:

| Subject | Sex | Age | Height | Weight | Metre 1 | Metre 2 | Metre 3 |
|---|---|---|---|---|---|---|---|
| A | F | 22 | 64" | 110 lbs | 663 | 662 | 663 |
| B | M | 15 | 65" | 127 lbs | 593 | 593 | 590 |
| C | M | 17 | 72" | 183 lbs | 429 | 429 | 429 |
| D | F | 20 | 61" | 135 lbs | 650 | 649 | 652 |
| E | F | 17 | 62" | 125 lbs | 669 | 665 | 664 |
| F | F | 49 | 62" | 175 lbs | 571 | 572 | 571 |
| G | F | 26 | 64" | 100 lbs | 709 | 710 | 708 |
| H | M | 30 | 78" | 216 lbs | 441 | 439 | 442 |
| I | M | 26 | 72" | 190 lbs | 461 | 461 | 458 |
| J | F | 27 | 67.5" | 126 lbs | 512 | 516 | 513 |
| K | M | 21 | 68.75" | 188 lbs | 443 | 443 | 442 |
| L | M | 24 | 70" | 155 lbs | 388 | 388 | 385 |
| M | F | 28 | 64" | 132 lbs | 545 | 543 | 543 |
| N | F | 19 | 67.5" | 144 lbs | 617 | 616 | 620 |
| O | M | 33 | 70" | 188 lbs | 411 | 411 | 411 |
| P | F | 31 | 71" | 162 lbs | 656 | 654 | 656 |
| Q | M | 21 | 63" | 145 lbs | 587 | 588 | 587 |

Standard Individual Error: 2 OHMs

TEST/RETEST DATA COMPARISONS

THE FOLLOWING DATA SPREAD SHEETS ARE THE RESULT OF "IN-HOUSE" TESTING TO DETERMINE THE ACCURACY OF TEST RE-TEST ON THE SAME BIO-OHM METRE THE SUBJECTS WERE CHOSEN FROM PATIENTS OF "LIVING WELL" IN TIGARD, OREGON

GROUP B:

| Subject | Sex | Age | Height | Weight | Test 1 | Re-Test |
|---|---|---|---|---|---|---|
| 1 | M | 23 | 70.0 | 166 | 490 | 487 |
| 2 | M | 20 | 76.0 | 199 | 388 | 382 |
| 3 | M | 31 | 73.0 | 217 | 423 | 423 |
| 4 | M | 25 | 69.0 | 201 | 376 | 378 |
| 5 | M | 23 | 71.5 | 223 | 354 | 348 |
| 6 | M | 22 | 70.0 | 188 | 433 | 433 |
| 7 | M | 19 | 65.3 | 175 | 387 | 387 |
| 8 | M | 20 | 69.0 | 163 | 489 | 492 |
| 9 | M | 27 | 71.5 | 198 | 422 | 417 |
| 10 | M | 22 | 65.4 | 167 | 354 | 354 |
| 11 | M | 21 | 67.75 | 156 | 367 | 367 |
| 12 | M | 21 | 71.5 | 211 | 405 | 407 |
| 13 | M | 23 | 73.75 | 189 | 381 | 378 |
| 14 | M | 19 | 70.0 | 176 | 361 | 361 |

FEMALES:

| | | | | | | |
|---|---|---|---|---|---|---|
| 1 | F | 31 | 65.5 | 133 | 623 | 625 |
| 2 | F | 26 | 67.5 | 143 | 665 | 664 |
| 3 | F | 30 | 62.0 | 112 | 544 | 521 |
| 4 | F | 23 | 65.25 | 119 | 567 | 567 |
| 5 | F | 21 | 61.0 | 103 | 707 | 705 |
| 6 | F | 19 | 58.75 | 92 | 772 | 771 |
| 7 | F | 20 | 65.5 | 144 | 615 | 612 |
| 8 | F | 20 | 66.0 | 132 | 598 | 602 |
| 9 | F | 23 | 68.5 | 123 | 576 | 580 |

STANDARD INDIVIDUAL ERROR: 1.5 OHMS

*Individual Sessions Same Day

FIG. 10

DATA LIST STATEMENT & TABLE

```
DATA LIST FILE = RAW/ID 1-3  SEX 5  HEIGHT 9-12 (2) RACE 7
                 WGTKGS 13-17 (2) H2OFAT 19-21 (1)
                 IMPFAT 31-33 (1) C1 35-36 C2 TO C5 37-48
                 C6 TO C11 49-60 C12 61-63 C13 TO C14 64-67
```

| REC | | | |
|---|---|---|---|
| 1 | 0 | | |
| 2 | 0 | | |
| 3 | 0 | | |
| 4 | 0 | | |

THE ABOVE DATA LIST STATEMENT WILL READ 1 RECORDS FROM FILE RAW

| VARIABLE | START | END | FORMAT | WIDTH | DEC |
|---|---|---|---|---|---|
| ID      | 1  | 3  | F | 3 | 0 |
| SEX     | 5  | 5  | F | 1 | 0 |
| HEIGHT  | 9  | 12 | F | 4 | 2 |
| RACE    | 7  | 7  | F | 1 | 0 |
| WGTKGS  | 13 | 17 | F | 5 | 2 |
| H2OFAT  | 19 | 21 | F | 3 | 1 |
| IMPFAT  | 31 | 33 | F | 3 | 1 |
| C1      | 35 | 36 | F | 2 | 0 |
| C2      | 37 | 39 | F | 3 | 0 |
| C3      | 40 | 42 | F | 3 | 0 |
| C4      | 43 | 45 | F | 3 | 0 |
| C5      | 46 | 48 | F | 3 | 0 |
| C6      | 49 | 51 | F | 3 | 0 |
| C7      | 51 | 52 | F | 2 | 0 |
| C8      | 53 | 54 | F | 2 | 0 |
| C9      | 55 | 56 | F | 2 | 0 |
| C10     | 57 | 58 | F | 2 | 0 |
| C11     | 59 | 60 | F | 2 | 0 |
| C12     | 61 | 63 | F | 3 | 0 |
| C13     | 64 | 65 | F | 2 | 0 |
| C14     | 66 | 67 | F | 2 | 0 |

END OF DATALIST TABLE

FIG. 15

ANTHRO-IMPEDANCE SITE MEASUREMENTS

A) INTRODUCTION

THE DATA ACQUISITION OF ANTHRO-IMPEDANCE VALUES REQUIRES THE USE OF A SPECIALIZED "ANTHRO-GAUGE" WHICH HAS THE QUANTITIVE CAPABILITY TO MEASURE LENGTH AND CIRCUMFERENCE VIA A CALIBRATED, CLOTH CENTIMETRE GAUGE. ALL ANTHRO-IMPEDANCE MEASUREMENTS SHOULD BE TAKEN WITH THE PATIENT IN THE STANDING POSITION IN A RELAXED STATE. MEASUREMENT SITES SHOULD BE EXPOSED FOR DIRECT MEASUREMENT. THE CLINICIAN SHOULD APPLY MINIMAL TENSION TO THE ANTHRO-GAUGE TO AVOID FAT AND ASSOCIATED TISSUE COMPRESSION. THE FOLLOWING DATA POINTS AND FORMULAS HAVE BEEN DEVELOPED AS A MEANS FOR MODIFYING THE CURRENT ALGORITHM EXPRESSION.

1.0 MALES 1.1 RIGHT ARM — MEASURE FROM THE AXILLA (UNDER THE ARM) TO THE TIP OF THE MIDDLE FINGER WITH THE PATIENTS ARM AT THEIR SIDE.

1.2 CHEST — MEASURE CHEST AT THE NIPPLES.

1.3 ABDOMEN — MEASURE THE PATIENTS ABDOMINAL CIRCUMFERENCE AT THE UMBILICUS.

1.4 RIGHT THIGH — THE RIGHT THIGH CIRCUMFERENCE IS MEASURED BENEATH THE GLUTEAL FOLD, NEAR THE BUTTOCKS.

1.5 RIGHT CALF — MEASURE THE MAXIMUM CIRCUMFERENCE OF THE PATIENTS RIGHT CALF.

1.6 CALCULATED VARIABLE FOR RIGHT THIGH / RIGHT CALF RATIO USED AS A DEPENDANT VARIABLE IN THE PROGRAM.

FIG. 16

ANTHRO-IMPEDANCE SITE MEASUREMENTS 2.0 FEMALES 2.1 NECK – MEASUREMENT TAKEN JUST BELOW THE THYROID CARTILAGE LOCATED IN THE MID-FRONTAL ASPECT OF THE NECK.

2.2 SHOULDERS – CIRCUMFERENCE MEASUREMENT ABOUT 1.5 INCHES BELOW THE ACROMION PROCESS LOCATED AT THE LATERAL SURFACE OF EACH SHOULDER.

2.3 ABDOMEN (1) – MEASUREMENT TAKEN AT THE SMALLEST CIRCUMFERENCE OF THE WAIST/ABDOMINAL REGION.

2.4 GLUTEUS – MEASUREMENT TAKEN AT THE LARGEST, MAXIMUM CIRCUMFERENCE OF THE BUTTOCKS REGION.

2.5 RIGHT THIGH – THE RIGHT THIGH MEASUREMENT IS TAKEN JUST BENEATH THE GLUTEAL FOLD NEAR THE BUTTOCKS.

2.6 ABDOMEN (2) – THE SECOND ABDOMINAL MEASUREMENT IS TAKEN AT THE UMBILICUS.

2.7 RATIO CALCULATION FOR SHOULDER/ABDOMEN 1

*FIG. 16A*

SEGMENTAL SITE PLACEMENT, ARM

SEGMENTAL SITE PLACEMENT, LEG

SEGMENTAL SITE PLACEMENT, TORSO

ANTHRO-IMPEDANCE INPUT    SCREEN: 3

Use the Anthro-Gauge to measure the patient's
circumferences at the selected measurement points.
Enter the measurements (in centimeters) below:

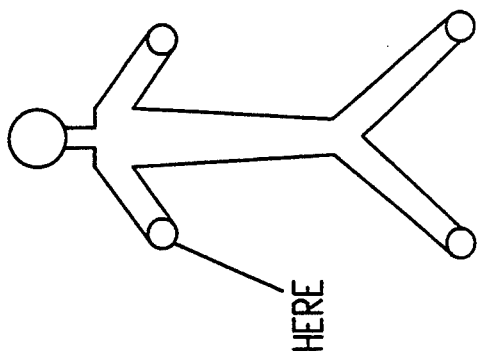

1) RIGHT ARM - measure from Axilla
   to tip of middle finger

2) CHEST - measure at nipples

3) ABDOMEN - measure at Umbilicus

4) RIGHT THIGH - just beneath the
   Gluteal Fold

5) RIGHT CALF - measure max. circ.

Press <F1> for HELP, <F5> to EXIT program, or <ENTER> after entry

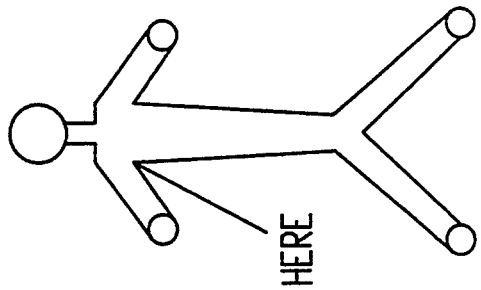

ANTHRO-IMPEDANCE INPUT     SCREEN: 3

Use the Anthro-Gauge to measure the patient's Circumferences at the selected measurement points. Enter the measurements (in centimeters) below:

1) RIGHT ARM - measure from Axilla to tip of middle finger

2) CHEST - measure at nipples

3) ABDOMEN - measure at Umbilicus

4) RIGHT THIGH - just beneath the Gluteal Fold

5) RIGHT CALF - measure max. circ.

Press <F1> for HELP, <F5> to EXIT program, or <ENTER> after entry

FIG. 23

ANTHRO-IMPEDANCE INPUT    SCREEN: 3

Use the Anthro-Gauge to measure the patient's
Circumferences at the selected measurement points.
Enter the measurements (in centimeters) below:

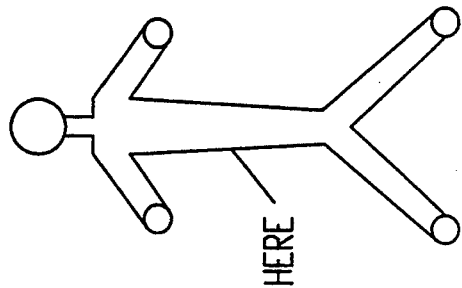
HERE

1) RIGHT ARM - measure from Axilla
   to tip of middle finger

2) CHEST - measure at nipples

3) ABDOMEN - measure at Umbilicus

4) RIGHT THIGH - just beneath the
   Gluteal Fold

5) RIGHT CALF - measure max. circ.

Press <F1> for HELP, <F5> to EXIT program, or <ENTER> after entry

FIG. 24

ANTHRO-IMPEDANCE INPUT        SCREEN: 3

Use the Anthro-Gauge to measure the patient's
Circumferences at the selected measurement points.
Enter the measurements (in centimeters) below:

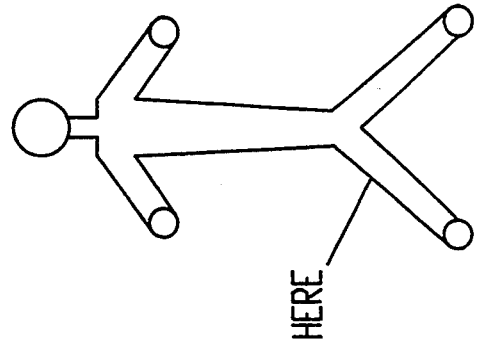
HERE

1) RIGHT ARM - measure from Axilla
   to tip of middle finger

2) CHEST - measure at nipples

3) ABDOMEN - measure at Umbilicus

4) RIGHT THIGH - just beneath the
   Gluteal Fold

5) RIGHT CALF - measure max. circ.

Press <F1> for HELP, <F5> to EXIT program, or <ENTER> after entry

FIG. 25

ANTHRO-IMPEDANCE INPUT    SCREEN: 3

Use the Anthro-Gauge to measure the patient's Circumferences at the selected measurement points. Enter the measurements (in centimeters) below:

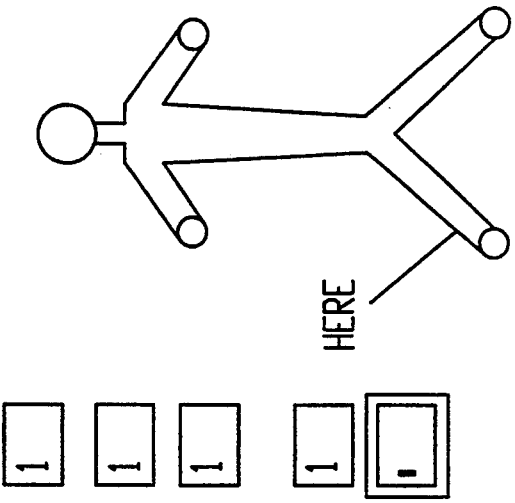
HERE

1) RIGHT ARM - measure from Axilla to tip of middle finger

2) CHEST - measure at nipples

3) ABDOMEN - measure at Umbilicus

4) RIGHT THIGH - just beneath the Gluteal Fold

5) RIGHT CALF - measure max. circ.

Press <F1> for HELP, <F5> to EXIT program, or <ENTER> after entry

FIG. 26

ANTHRO-IMPEDANCE INPUT   SCREEN: 4

Use the Anthro-Gauge to measure the patient's Circumferences at the selected measurement points. Enter the measurements (in centimeters) below:

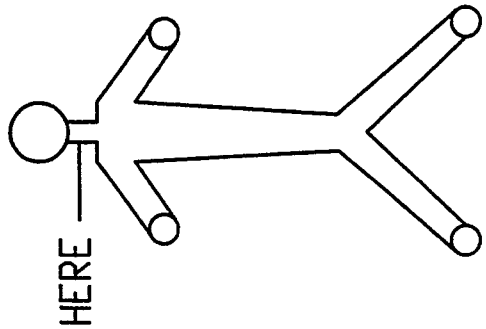
HERE

1) NECK - just below the thyroid cartilage
2) SHOULDERS - 1.5 inches below Acromion Process
3) ABDOMEN - at smallest circ.
4) GLUTEUS - measure max. circ.
5) RIGHT THIGH - just beneath the Gluteal Fold
6) ABDOMEN - measure at Umbilicus

Press <F1> for HELP, <F5> to EXIT program, or <ENTER> after entry

FIG. 27

ANTHRO-IMPEDANCE INPUT   SCREEN: 4

Use the Anthro-Gauge to measure the patient's Circumferences at the selected measurement points. Enter the measurements (in centimeters) below:

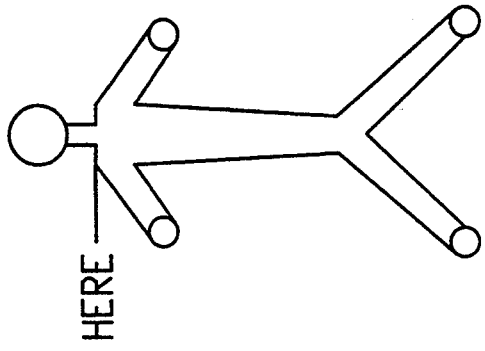
HERE

1) NECK - just below the thyroid cartilage
2) SHOULDERS - 1.5 inches below Acromion Process
3) ABDOMEN - at smallest circ.
4) GLUTEUS - measure max. circ.
5) RIGHT THIGH - just beneath the Gluteal Fold
6) ABDOMEN - measure at Umbilicus

Press <F1> for HELP, <F5> to EXIT program, or <ENTER> after entry

FIG. 28

ANTHRO-IMPEDANCE INPUT  SCREEN: 4

Use the Anthro-Gauge to measure the patient's Circumferences at the selected measurement points. Enter the measurements (in centimeters) below:

1) NECK - just below the thyroid cartilage  [1]

2) SHOULDERS - 1.5 inches below Acromion Process  [1]

3) ABDOMEN - at smallest circ.  [ ▯ ]

4) GLUTEUS - measure max. circ.  [ ]

5) RIGHT THIGH - just beneath the Gluteal Fold  [ ]

6) ABDOMEN - measure at Umbilicus  [ ]

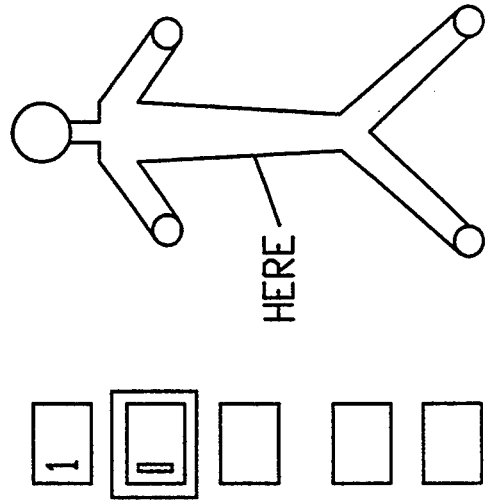
HERE

Press <F1> for HELP, <F5> to EXIT program, or <ENTER> after entry

FIG. 30

ANTHRO-IMPEDANCE INPUT
SCREEN: 4

Use the Anthro-Gauge to measure the patient's Circumferences at the selected measurement points. Enter the measurements (in centimeters) below:

1) NECK - just below the thyroid cartilage  [ 1 ]

2) SHOULDERS - 1.5 inches below Acromion Process  [ 1 ]

3) ABDOMEN - at smallest circ.  [ 1 ]

4) GLUTEUS - measure max. circ.  [ 1 ]

5) RIGHT THIGH - just beneath the Gluteal Fold  [ ▯ ]

6) ABDOMEN - measure at Umbilicus  [ ]

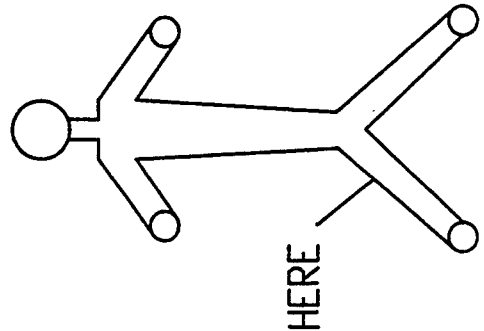

HERE

Press <F1> for HELP, <F5> to EXIT program, or <ENTER> after entry

FIG. 31

ANTHRO-IMPEDANCE INPUT  SCREEN: 4

Use the Anthro-Gauge to measure the patient's
Circumferences at the selected measurement points.
Enter the measurements (in centimeters) below:

1) NECK - just below the thyroid
   cartilage  [1]

2) SHOULDERS - 1.5 inches below
   Acromion Process  [1]

3) ABDOMEN - at smallest circ.  [1]

4) GLUTEUS - measure max. circ.  [1]

5) RIGHT THIGH - just beneath the
   Gluteal Fold  [1]

6) ABDOMEN - measure at Umbilicus  [0]

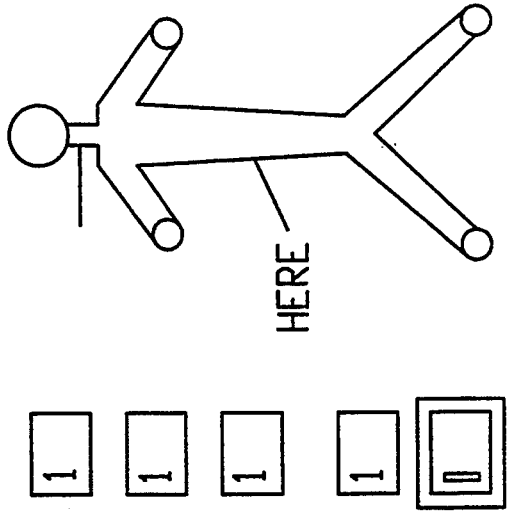
HERE

Press <F1> for HELP, <F5> to EXIT program, or <ENTER> after entry

SYSTEM FOR BODY IMPEDANCE DATA ACQUISITION UTILIZING SEGMENTAL IMPEDANCE & MULTIPLE FREQUENCY IMPEDANCE

CROSS REFERENCE TO RELATED APPLICATIONS

The present invention is a continuation-in-part application of the inventors' prior U.S. application Ser. No. 07/197,995, filed May 24, 1988, for SYSTEM FOR BODY IMPEDANCE DATA ACQUISITION, now U.S. Pat. No. 4,895,163.

BACKGROUND OF THE INVENTION

This invention relates to a system for conveniently and accurately measuring and quantitating the conductive potential of a human body which is based on a determination of lean tissue content. This new application further defines lean tissue content as Total Body Water (TBW) and allows differentiation of Total Water into extracellular mass (ECM) and intracellular or body cell mass (BCM).

Obesity has truly been declared, as of 1985 by the National Institute of Health, a stand-alone risk factor. In fact, obesity has been declared as a disease unto itself. It is now a new medical standard that obesity needs to be diagnosed and treated by a physician for the health and well-being of the general public.

A true definition of "obesity" has been difficult to define, in that such definition is dependent upon a percent body fat determination.

Historically, "percent body fat" has been determined in research laboratories by dunking people in a hydrostatic tank to perform a hydrostatic criterion method for quantification of body fat.

Hydrodensitometry (water tank immersion) has been generally considered to be the traditional standard for body composition analysis. Despite the biological and experimental errors inherent in hydrodensitometry (Lohman, T.G., Skinfolds and Body Density and Their Relation to Body Fatness: A Review, *Human Biology*, 53: 181–225), all other methods of analysis must be compared to it if they are to be validated.

Another known method for body fat analysis is skinfold measurement (calipers). However, many skilled health care practitioners have questioned this methodology for body composition analysis in that reliability is doubtful. In the hands of trained technicians, anthropometry can give errors of plus or minus nine percent (9%) when compared to densitometry (Katch, F.I., Katch, V.L. (1980), Measurement and Prediction Errors in Body Composition Assessment and the Search for the Perfect Equation. *Research Quarterly for Exercise and Support*, Vol. 51, No. 1, 249–260). In general clinical use in the hands of a variety of trained examiners with less than expert skill, the error in the caliper technique is presumably even greater.

Recently, body composition analyzers have been introduced that utilize a relatively new technology known as tetrapolar bio-electrical impedance.

Most importantly, through tetrapolar bio-electrical technology, the test/retest reliability has been reported as 0.5% (Lukaski, H.C., Johnson, P.E., Bolonchuck, W.W., and Lykken, G.I., Assessment of Fat-Free Mass Using Bio-Electrical Impedance Measurements of the Human Body) compared to a test/retest reliability of 3.8% for hydrodensitometry.

In this respect, the human body is composed basically of two components—one is lean body mass (Lean Body Mass=Total Body Water+the other listed tissue, Total Body Water=Extracellular mass+body cell mass), which is composed of muscle tissue, connective tissue and bones; and the other major component is body fat. Bio-electrical impedance technology quantifies the true ratio of these components-the difference between lean body mass, which is the healthy metabolizing part, and the body fat, which is the storage of energy in your body. Lean body mass has about 75% water; in contrast, fat is about 3% to 13% water. Accordingly, bio-electrical impedance technology measures the "healthy" part of the body, which is the lean body mass. Lean body mass can also be called Total Body (TBW)+other listed tissues. Total body water is comprised of extracellular mass (ECM) and body cell mass (BCM).

While known tetrapolar bio-electrical technology is considered by many to be an advance from hydrodensitometry both from a reliability standpoint and convenience standpoint, known impedance systems have produced inaccurate body composition analysis in that such known systems are dependent upon a linear regression equation approach. Moreover, much of the data derived from known bio-electrical impedance techniques fails to consider biological data of specific patient groups which may deleteriously affect the accuracy of the body composition analysis.

Accordingly, those skilled in the art have recognized a significant need for an accurate, efficient, valid measurement approach to human body composition quantification. The present invention provides a procedure for quantitative measurement of the conductive potential of the body in a convenient and reliable manner, then through program generated computer screens, solicits sex specific circumference and limb length measurements, and then provides the means for modifying the body impedance measurement with newly created algorithm formula equations that generate scientifically validated predictions of human body composition analysis. The present invention allows the quantification of human fitness or obesity to occur on a significantly wider and more accurate scale than previously achieved.

In addition, the present invention in certain circumstances, includes the gathering of segmental impedance signals and/or multiple, variable frequency impedance measurements. This aspect of the present invention allows the further definitions of body composition into subsets of Total Body Water. The specific means for modifying segmental impedance and/pr multiple variable frequency impedance allows for the objective nutritional and hydration analysis in the outpatient, inpatient and intensive care settings.

SUMMARY OF THE INVENTION

The unique system of the present invention provides an accurate valid measurement of human body composition consisting of fat tissue, lean tissue and body water. The inventive methodology provides a procedure for quantitative measurement of the conductive potential of the body, which is based on the lean tissue (including Total Body Water) content of the body, in a convenient and reliable manner. Further, the system differentiates two components of Total Body Water which are Extracellular Mass (ECM) and Body Cell Mass (BCM).

This embodiment of the invention is based on further defining the measurement of Total Body Water (TBW) through the use of segmental impedance and multiple, variable frequency impedance measurements.

Total Body Water (TBW) is defined as Body Cell Mass (BCM=intracellular water) plus Extracellular Mass (ECM=extracellular water). There is significant medical and paramedical value in being able to define the BCM and ECM compartments of TBW in various individuals and in being able to measure changes in these compartments in one individual over time.

For example, the present invention offers the ability to measure and quantify acute or chronic dehydration or over hydration of patients, either in one measurement or in multiple measurements over time. These embodied quantifications allow for proactive medical treatment of various defined hydration conditions, minimizing the negative impact of these abnormal clinical states.

SEGMENTAL IMPEDANCE MEASUREMENTS

In this expanded application of the invention, in addition to total body Impedance, impedance measurement are taken with application of sensors on the anatomically defined extremes of certain segments of the human body. The segments in this claim include but are not limited to: 1) the right arm 2) the right leg and 3) the torso. These bioimpedance signal measurements are generated by the currently allowed system. These newly defined measurements are then processed by unique, research derived software driven formulae which analyze relationships and changes in relationships between total body impedance and segmental impedance values. These relationships and changes in relationships can be qualified and quantified as a certain distribution and/or changes in distribution of the ECM and BCM compartments of Total Body Water (TBW). Certain derived formulae methods within this expanded application are utilized as a unique means of modifying the various bioimpedance signals.

MULTIPLE FREQUENCY IMPEDANCE

In the invention, a single, predetermined frequency of about 40 to 60 kilohertz has been demonstrated to be the appropriate current for accurate and precise measurement by the allowed system of Total Body Impedance. And, Total Body Impedance (conductivity) is directly related to the calculation of Total Body Water.

Research conducted since the original invention reveals that multiple, variable frequencies within the range of about 5 kilohertz to about 150 kilohertz generated and displayed by the invention, facilitate further analysis of Total Body Water and its subsets of extracellular water (ECM) and body cell mass (BCM=intracellular water).

Specifically, when two (or more) frequencies are utilized in the same patient test session, these two (or more) measurements (in ohms) allowed predictive analysis of ECM and BCM. Further, sequential analysis over time of the same patient with two (or more) frequencies, when analyzed by the new software driven means for modifying formulae allows predictive output that qualifies and quantifies changes in ECM versus changes in BCM. The method of these new means for modifying formulae as well as the modified method of introducing multiple, variable bioimpedance frequencies are part of this expanded application.

Additionally, this invention includes those formulae that combine segmental data, multiple frequency data, and anthropomorphic data.

In accordance with the present invention, improved algorithm formulae are provided to define an appropriate individual on set of variable. These new, unique formulae allow the variable input of specific total body impedance, segmental impedance, multiple frequency measurements and derived anthropomorphic data to give a more complete, predictive ability in amazing static and dynamic volume conditions within the total body water compartment.

The data generated by these expanded claims and the additional means for modifying the data from the invention and the expanded system described in this application offers the opportunity for significantly better medical management of patient nutrition and hydration status in outpatient, inpatient and intensive care diagnostic and treatment scenarios.

In more detail, the quantitative measurement in accordance with the present invention is referred to as a "bio-impedance signal." This electrical signal, in ohms, is derived from a means for measuring body and segmental impedance component of the system. The resultant signals (three digit number, between 1 and 1000 ohms) is then entered into a modifying means component to accurately predict the body composition of the tested individual.

The unique modifying means, in one embodied form, comprises prediction formulas derived from biological data inputs including: a patient's height, weight, age and sex, to determine a "population prediction variable."

Thus, the unique modifying means of the inventive system interprets bio-impedance readings as "population specific", i.e., specific impedance values are exhibited by various pre-defined populations of individuals. This specificity is related to morph-type, leanness, body water and age. In accordance with the present invention, an algorithm formula approach to prediction formulas is utilized to define an appropriate individual into a set of population specific variables.

Initially, the bio-impedance signal is imputed into the modifying means along with biological data. In the present unique means, this data includes sex specific anthropometric measurements, as well as segmental impedance and multiple, variable frequency impedance. Thereafter, algorithm formulas modify the imputed signals by the appropriate correction factor. The correction factor is generally non-linear and derived from comparison with known hydrostatically derived values to produce an output. The output is thereafter entered by the software into a second set of unique formulas to produce a "research" level of scientifically valid results. The results may then be conveniently displayed by indicator means so that multiple compartment body composition can be predicted.

SEGMENTAL IMPEDANCE

The current bio-impedance claims are based on the measurement of total body impedance which is directly related to Total Body Water. Total Body Water is defined as Body Cell Mass, (BCM or Intra-cellular Water) and Extra Cellular Mass, (ECM or Extra Cellular Water). Through the measurement of Total Body Water, human body composition is predicted.

The current claim includes citation of sensor placement on the right hand and right foot which represents the furthest anatomical points at which total body impedance may be quantified thus predicting total body water from the biopedance signal of about 40 to 60 kilohertz.

The segmental measurement approach places sensors on the anatomical extremes on each of the body segments. The segments are 1) right leg 2) right arm and 3) torso, the C.I.P. claim for modification is that the qualitative measurement of these body segments and the changes that occur between them can be used to predict the accumulations of body fluids into ECM and the BCM spaces.

As body fluid is osmotically moved or fluid accumulation occurs in the extra cellular spaces, bio-impedance changes between the segments occurs. The accumulation of fluids produces different changes in the bio-impedance relationship between the segments. These changes can be qualified as distributional changes of total body water between carious Intra-Cellular (BCM) and Extra-Cellular (ECM) compartments of the body.

The torso, due to it's physiological role exhibits more varied changes in cio-impedance than the leg or arm segment. Due to lower extremity pooling of fluids related to hydrostatic and gravitational pressures, the leg segment may also exhibit extreme changes in bio-impedance signals.

As the ECM fluids begin to accumulate, the bio-impedance signal decreases in value because the segment being measured has an increase in conductive potential due to the increase in fluid volume. Increases in segmental fluid volume will decrease bio-impedance values. Decreases in segmental fluid volume will decrease the conductive potential and thus increase the bio-impedance value.

Specific application of bio-impedance segmental measurements is in the field of OB/GYN. During the third trimester of pregnancy some individuals begin to "pool" or increase extra cellular fluid volume. This phenomenon can lead to a fatal condition known as pregnancy induced hypertension (PIH).

The results of a recent study of PIH concluded that the use of segmental bio-impedance described a characteristic alteration of body water distribution especially in the lower extremity allowing the physician to monitor the degree and severity of fluid accumulation with segmental bio-impedance measurements and make diagnostic and prescriptive assumptions to proactively treat the patient before PIH manifests.

MULTIPLE FREQUENCY

The current claim on a single, pre-determined frequency of about 40 to 60 kilohertz has been demonstrated to be an accurate and precise predictor or total body impedance. Frequencies or about 40 to 60 kilohertz are considered to be medium frequency bio-impedance signals. Total Body Impedance is used in various equations to predict the relationship between Total Body Water (TBW), Lean Body Mass (LBM) and Total Body Fat (TBF) in the individual patient.

Recent Developments reveal that through multiple frequencies of higher and lower kilohertz signals other physiological assumptions can be made such as fluid distribution between ECM and BCM as well as hydration status. The current assumption is that a single frequency of about 40 to 60 kilohertz is specifically measuring Total Cell Mass (TCM) or the sum of the Body Cell Mass (BCM) and Extra Cellular Mass (ECM).

LOW FREQUENCY BIO-IMPEDANCE SIGNALS

Lower bio-impedance frequencies of about 15 to 35 kilohertz are thought to be carried by Extra Cellular Masses (ECM). Due to membrane physiology, fluid distribution and electrolyte content, the use of low frequency bio-electrical currents detect more sensitive changes in ECM. Sixty percent of Total Body Water is through to be maintained in the ECM spaces, changes in ECM volume can be used to predict hydration status in an individual which can be important in many medical protocol.

Thus, the relationship between Total Body Water, derived from the current medium frequency of about 40 to 60 kilohertz, and Extra Cellular Mass, derived from the lower frequency claim of about 15 to 35 kilohertz can be used to determine total fluid volume more precisely than the current single frequency signal.

HIGH FREQUENCY BIO-IMPEDANCE SIGNALS

The use of a bio-impedance frequency of higher than about 40 to 60 kilohertz are though to "saturate" the Total Cell Mass and have no better prediction correlations than a frequency of about 40 to 60 kilohertz. However, some individuals present a physiology which is resistant to or exhibits a "shunting effect" of the medium frequency signals, thus creating prediction errors for total composition based on a measurement error of Total Body Impedance. This type of individual with abnormal physiology can be more precisely predictive for Total Cell Mass and thus Total Body Water with a higher bio-impedance frequency signal of about 100 to 150 kilohertz.

The higher bio-impedance frequencies of about 100 to 150 kilohertz have little or no bio-electrical effect on individuals with normal physiology yet increase membrane permeability on individuals with abnormal physiology giving better predictive value for both body composition and fluid distribution.

It will be appreciated from the foregoing that the present invention provides an accurate and convenient system for quantifying body fat as a percentage of weight which is an important health management tool for patient and physician alike, as well as for use in the research setting. In addition, the ability to predict ECM and BCM and changes in these fluid compartments offers the opportunity for superior medical management of patient nutrition and hydration status. Other features and advantages of the present invention will become apparent from the following, more detailed description, taken in conjunction with the accompanying drawings, which illustrate by way of example the principles of the invention.

BRIEF DESCRIPTION OF THE DRAWINGS

FIG. 9 is a perspective view of a suitable computer in accordance with one embodiment of the present invention;

FIG. 10 is a chart of tests/re-test data comparison in accordance with the present invention;

FIG. 11 is a chart of inter-meter comparisons in accordance with the present invention;

FIG. 15 is a data list statement and table referred to in Example I in accordance with the present invention;

FIGS. 16 and 16A are AnthroImpedance site measurements for males and females in accordance with the present invention.

FIG. 21 is a depiction of an anthroimpedance input on a display screen in accordance with the present invention;

FIG. 22 is a depiction of an anthroimpedance input on a display screen in accordance with the present invention;

FIG. 23 is a depiction of an anthroimpedance input on a display screen in accordance with the present invention;

FIG. 24 is a depiction of an anthroimpedance input on a display screen in accordance with the present invention;

FIG. 25 is a depiction of an anthroimpedance input on a display screen in accordance with the present invention;

FIG. 26 is a depiction of an anthroimpedance input on a display screen in accordance with the present invention;

FIG. 27 is a depiction of an anthroimpedance input on a display screen in accordance with the present invention;

FIG. 28 is a depiction of an anthroimpedance input on a display screen in accordance with the present invention;

FIG. 30 is a depiction of an anthroimpedance input on a display screen in accordance with the present invention; and FIG. 31 is a depiction of an anthroimpedance input on a display screen in accordance with the present invention.

DESCRIPTION OF THE PREFERRED EMBODIMENTS

Figure 1:
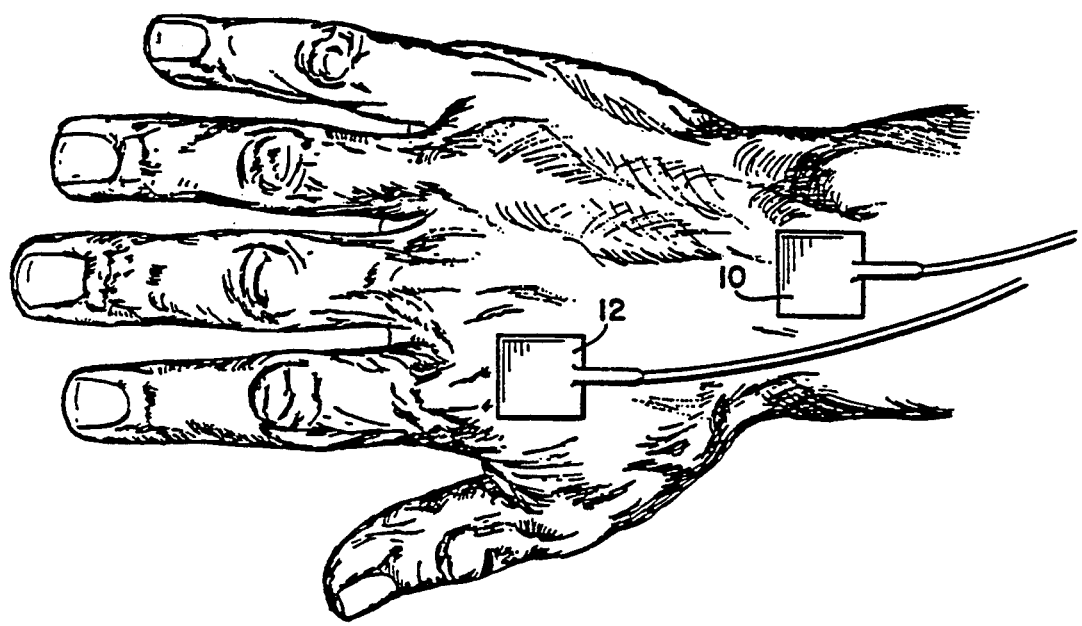
FIG. 1 is a perspective view of first and second prescribed locations for locating electrode sensors in accordance with one embodiment of the present invention.

As shown in the drawings for purposes of illustration, the present invention is embodied in a unique system for acquisition of body impedance date, which comprises in combination:

a) a plurality of electrode sensors for mounting to prescribed locations; of a patient's body to be analyzed;

b) mounting means for removably attaching said electrode sensors to a Kelvin Bridge bio-impedance meter system having four terminal leads;

c) means for generating a current flow through said electrode sensors at a variable frequency of from about 5 Kilohertz to about 150 Kilohertz, thereby producing an output range of 0 to 1,000 ohms for each frequency measured.

d) means for generating input variables comprised of biological patient data including, height, weight, age, and sex and bio-impedance signal levels to determine population specific variable;

e) means for manipulating said electrical signals derived from said means for generating a body impedance signal with said population prediction variable;

f) indicator means for displaying said resultant output signal to provide quantitative measurement of conductive potential of said patient's body based on Total Body Water content of said patient;

g) means for comparing said resultant signal with known scatter grams to produce an output signal representative of fat tissue, lean tissue and total body water; and h) second means for comparing data derived from step (g) with known anthropometric data to produce an output signal representative of fat, tissue, lean tissue and body water.

In more detail, the anthropometric data of step (h) includes, circumference and limb length measurement measures were obtained on 769 subjects and unique prediction equations have been developed. The unique equations comprise a series of circumference measurements and limb measurements and ratios which are incorporated with bioelectrical impedance signals to more accurately determine percent body fat. This combination of anthropometric and bioimpedance substantially improved both validity coefficients as well as SEE as can be seen in Exhibit 1.

Thus, the improved means of the present invention provides a novel software controlled system that can generate human body composition results at either a "clinical" or "research" level of accuracy. i-third means for comparing and modifying data from steps g and h where segmental impedance data and multiple, variable frequency impedance data is utilized to predict Total Body Water, Extracellular Body Mass and Body Cell Mass.

In accordance with the present invention, an electrical Kelvin Bridge is created by a plurality of electrodes which are removably attached to specific body areas. In more detail, prior to sensor placement, each body location is palpated and preferably cleaned with an alcohol swab to remove skin or surface oils. Thereafter, each electrode sensor is placed on a patient's body. Preferably, a conductive gel is utilized to temporarily hold the sensor in place.

ELECTRODE SENSOR LOCATIONS—TOTAL BODY IMPEDANCE (1) The first prescribed location 10 is the back side of the patient's right hand. ("Dorsal Aspect.") Locate the "Styloid Precess." (The 'bump' near the back of the wrist.) Palpate approximately 0.5 to 1 inch directly across from the "Styloid Process." (Note the slight 'depression' between the "Radius" and "Ulna.") The First Sensor is placed across from the "Styloid Process" in the middle of the wrist. (The Sensor center should be directly over the slight 'depression' described above.) Note: Placing the electrodes so they 'point' away from the body is recommended. (See FIG. 1)

(2) The second prescribed location 12 is behind the knuckle (joint) of the index finger of the right hand. ("Distal end of the second metacarpal.") Palpate this area. Place the Second Sensor directly on the hand behind, but not touching, the right index finger. (See FIG. 1)

Figure 2:
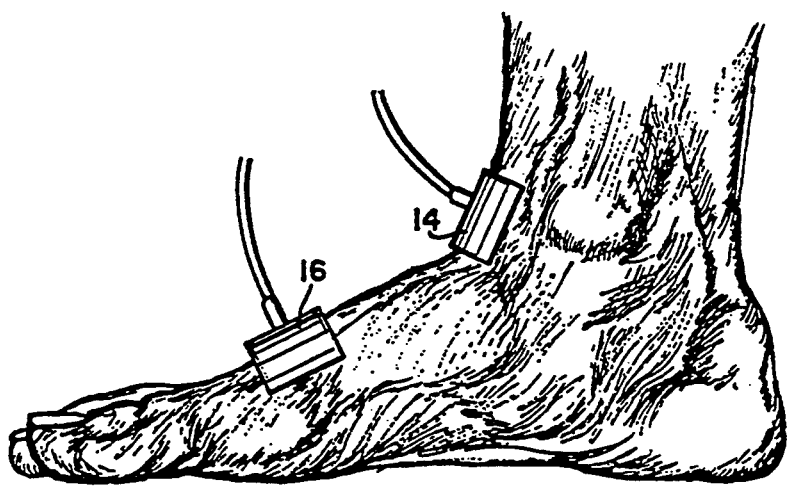
FIG. 2 is a perspective view of second and third prescribed locations for locating electrode sensors in accordance with one embodiment of present invention.

(3) The third prescribed location 14 is the patient's ankle at the front of the right foot. (Inbetween the "Medial" and "Lateral Malleoli"—the 'bumps' on the inside and outside of the ankle.) Note the slight 'depression' in this area where the ankle meets the top of the foot. Palpate here. Place the Third Sensor so that its center directly covers the slight 'depression' described above. (See FIG. 2)

(4) The fourth prescribed location 16 is the top of the right foot behind the joint of the great toe. (The "Distal" portion of the first "metatarsal.") Palpate this area. Place the Fourth Sensor on the top of the right foot, behind, but not touching the great toe. (See FIG. 2)

SEGMENTAL SITE PLACEMENT 1.0 Segmental Sensor Site Placement 1.1 Right Leg 1.1.1 Right foot distal ground sensor (black lead) and proximal signal sensor (red lead) have the same anatomical location as the standard technique.

1.1.2 The second set of leads are placed on the upper thigh region with the distal ground sensor (black lead) placed over the protuberance of the greater trochanter of the femur, the greater trochanter is located at the tip of the hip, The proximal signal sensor (red lead) is placed located exactly two (2) inches from the leading edge of the distal ground sensor (black lead) located over the greater trochanter. This is a standard sensor placement procedure for all patients to insure test re-test reproducibility.

1.2 Right Arm 1.2.1 The right hand distal ground sensor (black lead) and proximal signal sensor (red lead) have the same anatomical location as the standard technique.

1.2.2 The second set of leads are placed on the upper arm region near the shoulder. The acromion process is the site of the distal ground sensor (black lead). The acromion process is located at the tip of the shoulder at the shoulder joint. The proximal signal sensor (red lead) is located exactly two (2) inches from the leading edge of the distal ground sensor located on the acromion process. This is a standard sensor placement for all patients to insure test re-test reproducibility.

1.3 Torso/Abdomen 1.3.1 The first set of leads are placed on the upper thigh region with the distal ground sensor (black lead) placed over the protuberance of the feather trochanter of the femur, the greater trochanter is located at the tip of the hip. The proximal signal sensor (red lead) is placed located exactly two (2) inches from the leading edge of the distal ground sensor (black lead) located over the greater trochanter. This is a standard sensor placement procedure for all patients to insure test re-test reproducibility.

1.3.2 The second of leads are placed on the upper arm region near the shoulder. The acromion process is the site of the distal ground sensor (black lead). The acromion process is located at the tip of the shoulder at the shoulder joint. The proximal signal sensor (red lead) is located exactly two (2) inches from the leading edge of the distal ground sensor located on the acromion process. This is a standard sensor placement for all patients to insure test re-test reproducibility.

POWER SUPPLY

Figure 3:
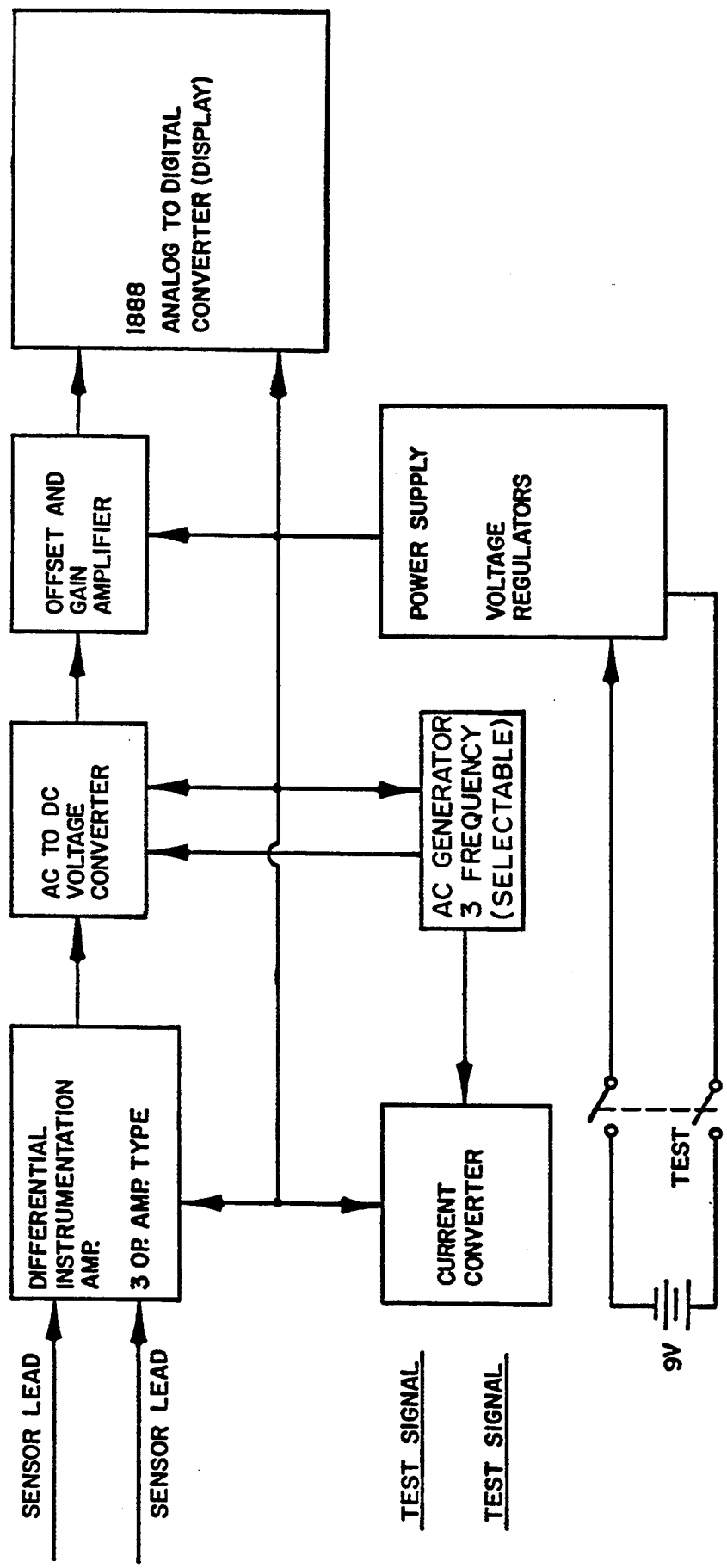
FIG. 3 is a schematic block diagram depicting one embodied form of the inventive system for body impedance data acquisition in accordance with the present invention.
Figure 5:
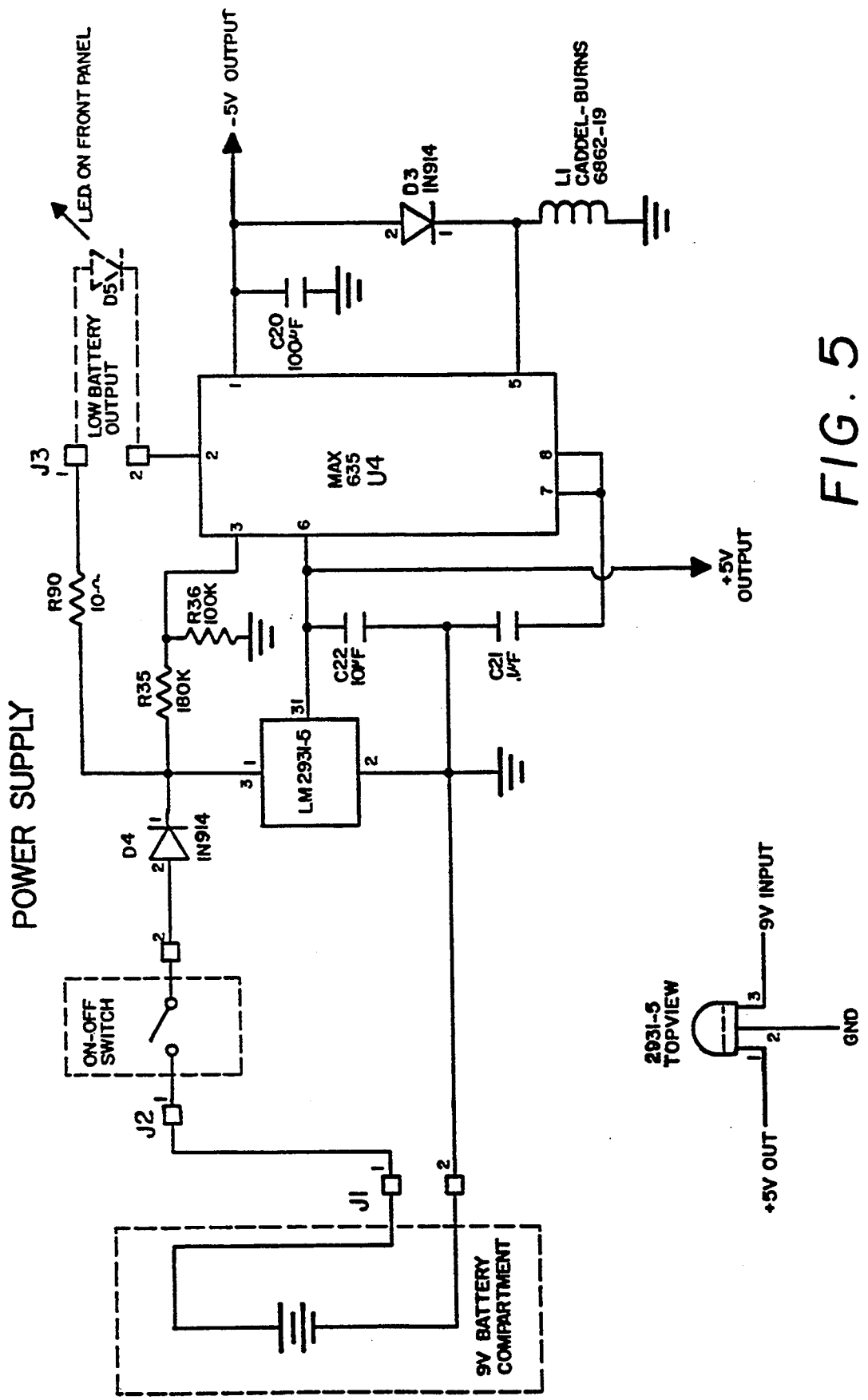
FIG. 5 is a circuit diagram of a power supply for the inventive system in accordance with one embodied form of the invention.

The power supply for the inventive system is preferably provided by a single nine (9) volt alkaline battery (See FIGS. 3 and 5). The circuit pathways are designed for safety and efficiency. A momentary on and off power switch is used to conserve battery life. The bio-impedance metre test life expectancy is 500 tests.

The design of the power supply circuit allows a test signal and a sensor circuit to operate within given parameters without being dependent upon a specific battery change level. Diode protection is preferably provided both at the power source and at the power input section of the printed circuit board to insure against reverse current flow.

To maintain an optimal functioning range, the system generates a 5 volt charge to power the sensor and digital functions.

To provide a reliable and viable power source, a low battery (LED) is displayed when the current power source (9 volt battery) drops below 6.2 volts.

The power drain of the LED will consume the remaining voltage within 30 seconds. Note: The average commercial grade 9 volt alkaline battery is charged at 9.2 volts.

MEANS FOR GENERATING BODY IMPEDANCE SIGNAL

Preferably one 9-volt battery operates the means for generating body impedance signal. The technology utilizes a Kelvin Bridge system with 4 terminal leads. The Sensors previously described attaches to each terminal end and is placed on the patient for correct data Impedance acquisition.

OPERATION

As described, the body impedance system generates a frequency which is totally undetectable to the human body.

After checking that the four electrode sensors are properly placed, the patient remains prone and still.

The on/off switch is placed in the "on" position. The Meter takes Impedance readings at a rate of 50,000 times per second. Often the Meter takes 1 to 3 seconds to stabilize while 'searching' for the most accurate reading. Several factors such as subcutaneal fat thickness, skin thickness and body hair account for slower impedance readings.

TECHNICAL SPECIFICATIONS

The preferred technical specifications of the means for generating body impedance system are as follows:

| | |
|---|---|
| a) Device test signal current - | about 800 microamps nominal; |
| b) Device test variable signal - frequency | between about 5K#2 and 150 KHZ nominal; |
| c) Input range - | 0 to 1000 ohms; |
| d) Input impedance - | about 10 meg ohm; |
| e) Accuracy - | about 1%; |
| f) Supply current (qeiecent) - | about 70 MA nominal; |
| g) Negative supply battery range - | about 8.5 to 10 volts; |
| h) Positive supply battery range - | about 8.5 to 10 volts; |
| i) Battery polarity protection - | Dual diode. |

SCHEMATIC DIAGRAM

Figure 7:
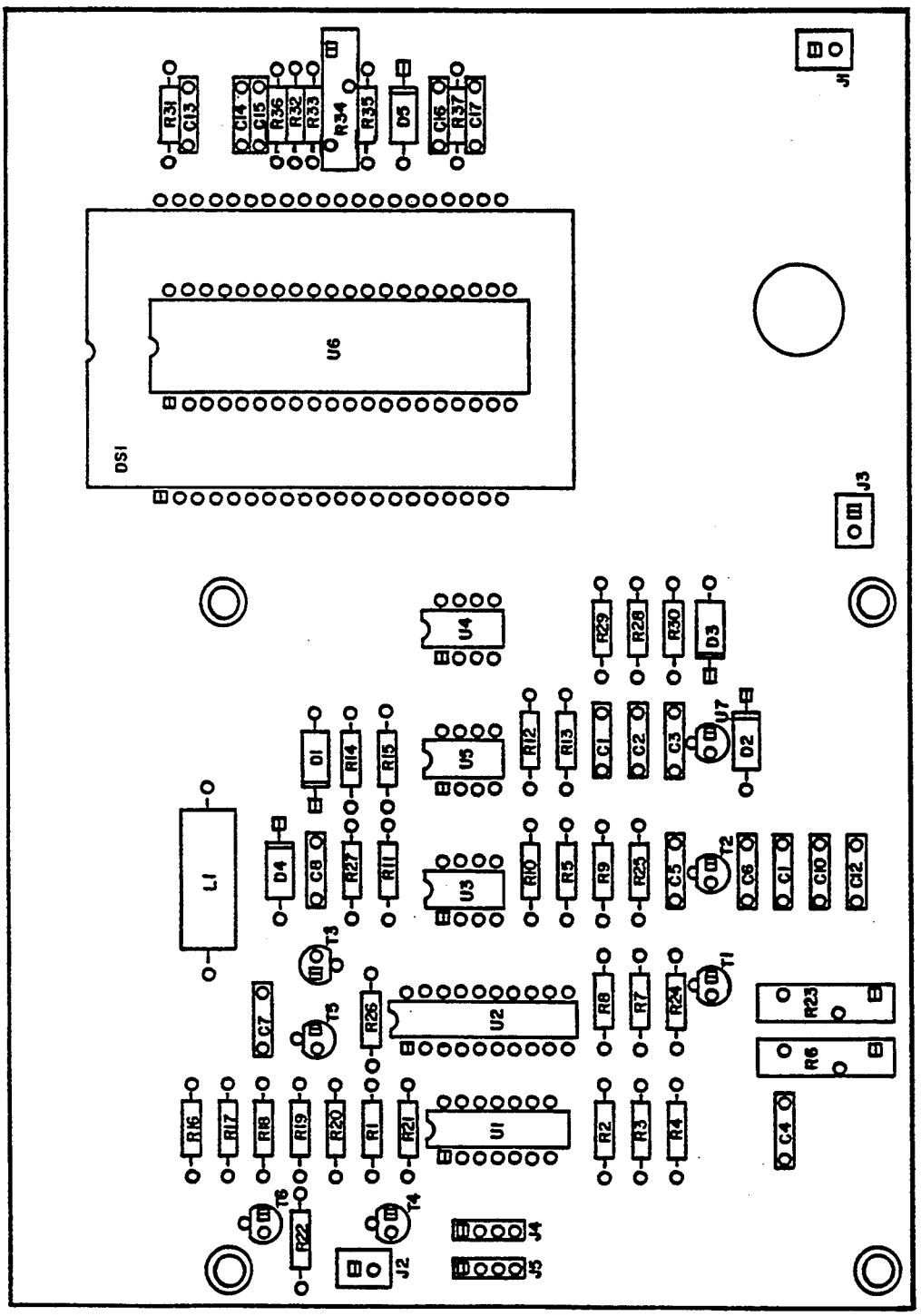
FIG. 7 is an electrical circuit diagram of a pin-out diagram of a body impedance meter in accordance with one embodiment of the present invention.

The pin-out diagram illustrated in FIG. 7 details one embodied printed circuit board for the means for generating body impedance system.

The details of the schematic are presented in the following sections:

1) Sensor circuit; and
2) Test signal generation.

Each of these sections will refer to block diagrams to highlight the exact electronic configuration.

3) Frequency selector.

SENSOR CIRCUIT

Figure 6:
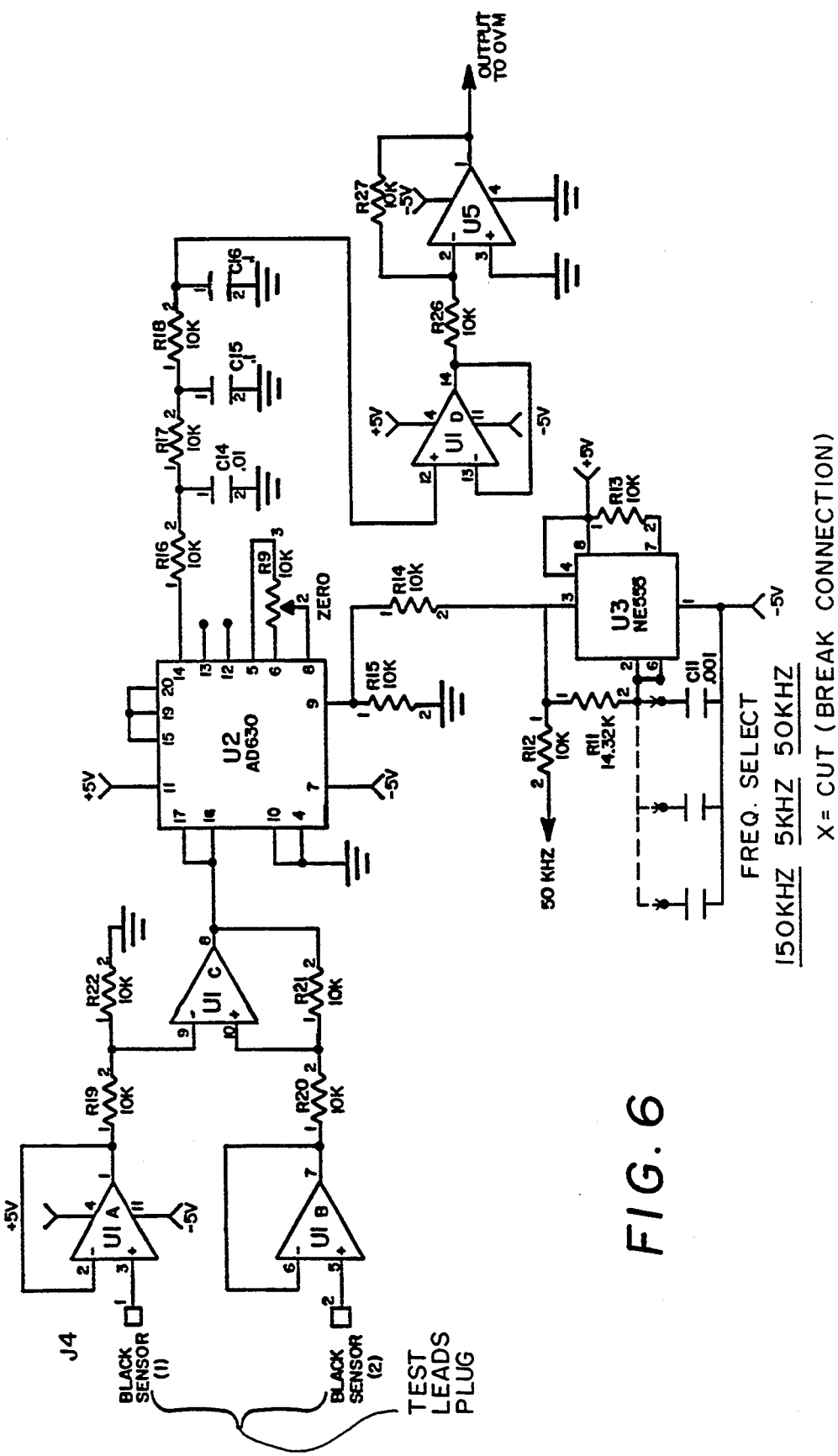
FIG. 6 is a circuit diagram of a sensor circuit in accordance with one embodied form of the present invention.

FIGS. 3 and 6 are block diagrams detailing one embodied sensor circuit of the impedance meter. The electronic circuitry and components include the analog to digital (A to D) technology. To obtain valid bio-impedance measurements, a true tetra—polar bridge system must be employed. The circuit in application provides a tetra-polar bridge (four lead bridge).

The sensor circuit preferably operates at an 800 microamp level. The sensor current combined with the test signal generation, powers the inventive system.

As outlined previously, the bio-impedance analyzer is connected to the body by four leads, two connected to the right hand and two to the right foot. The sensing current is then placed between the poles.

TEST SIGNAL GENERATION

Figure 4:
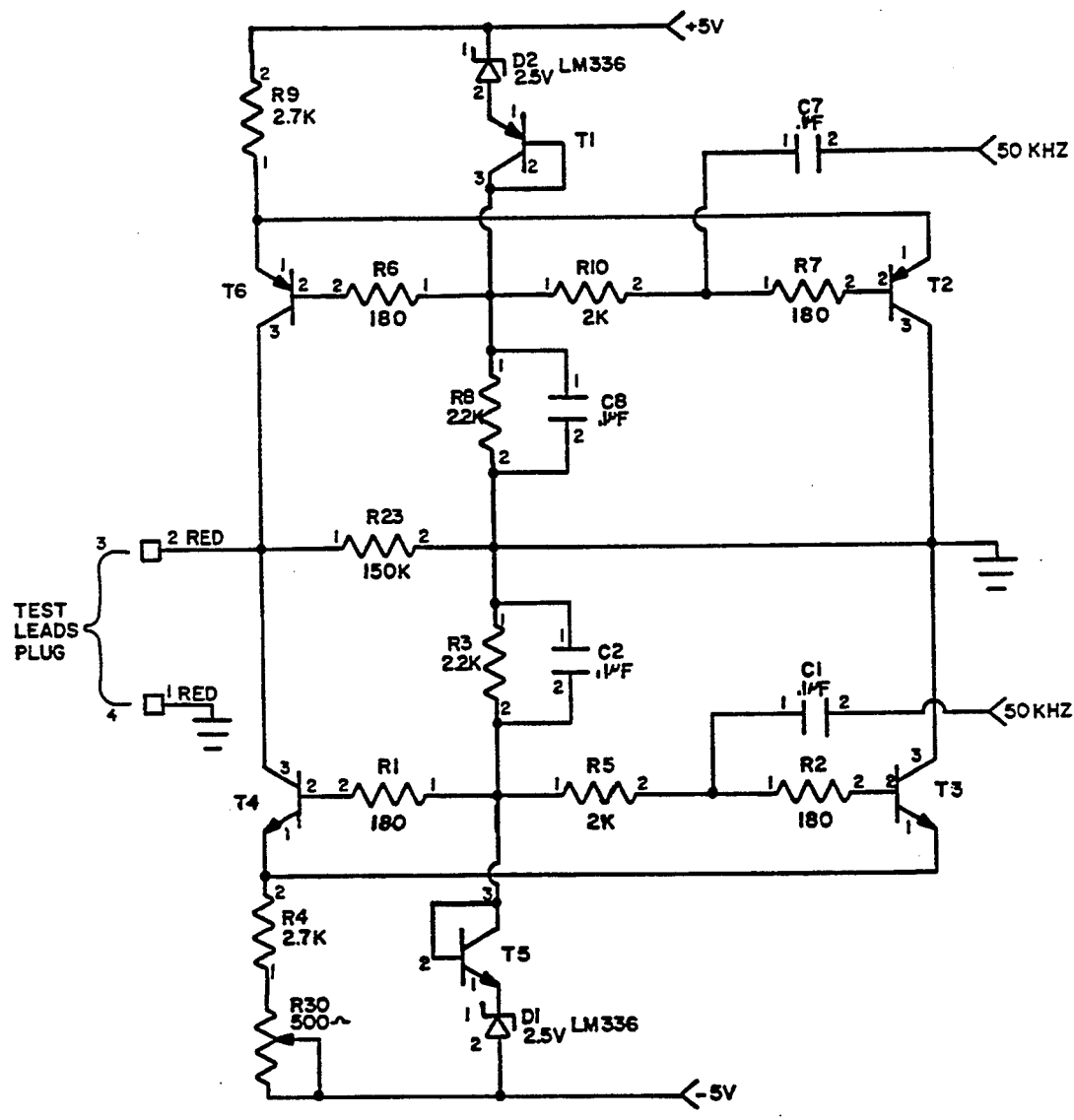
FIG. 4 is a circuit diagram of a test signal generator in accordance with one embodiment of the present invention.

A variable test signal is maintained through the components with a frequency of between 5 to 150 Kilohertz and preferably at 15-50-150 KiloHertz. The block diagram illustrated by FIGS. 3 and 4 details the specifications and current flow of the bio-impedance analyzer.

The test signal configuration is calibrated at the 500 ohms level, selected as a mid-point in the bio-impedance analyzer reading scale of 1 to 1000 ohms.

The test signal generator remains constant due to the constant voltage of 5 volts from the power supply. A constant power supply of 5 volts is critical for the reproducibility of data obtained from the bio-impedance analyzer. A low battery indicator calibration for 6.2 volts ensures a constant 5 volt current source.

MODIFICATION OF IMPEDANCE SIGNALS

The raw electrical signals from the impedance meter are modified by a prescribed correlation factor of body density and to predict body composition.

$$(BD = 1.14111 - 0.0763 \ (weight) \ (impedance/height^2)).$$

Based on a given body density a "range of impedance readings" is expected. This range is population specific. Thus, once body density is derived and compared to impedance, a constant is then selected for the body analysis formula.

Figure 8:
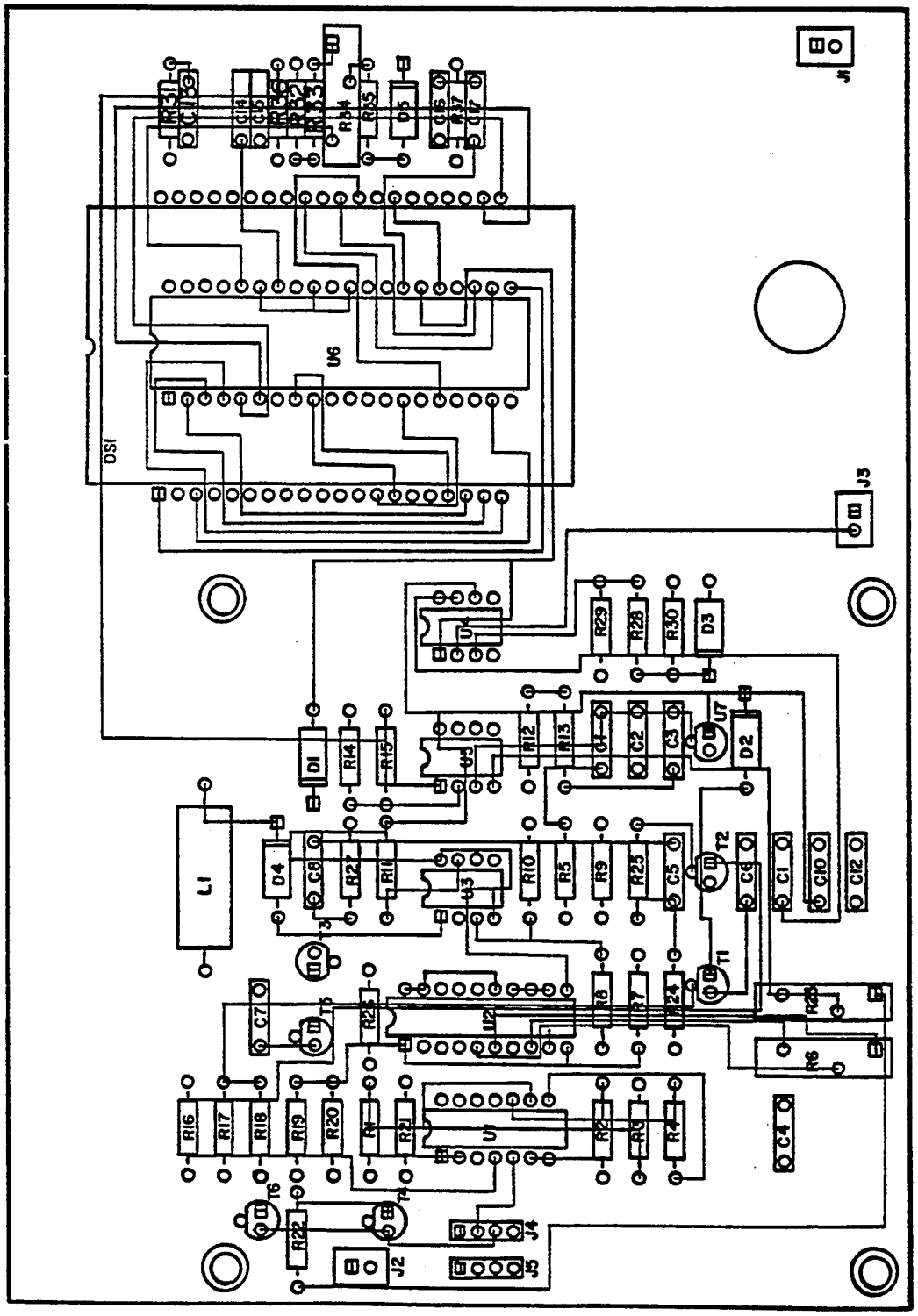
FIG. 8 is a schematic in more detail of a body impedance meter in accordance with one embodiment of the present invention.
Figure 12:
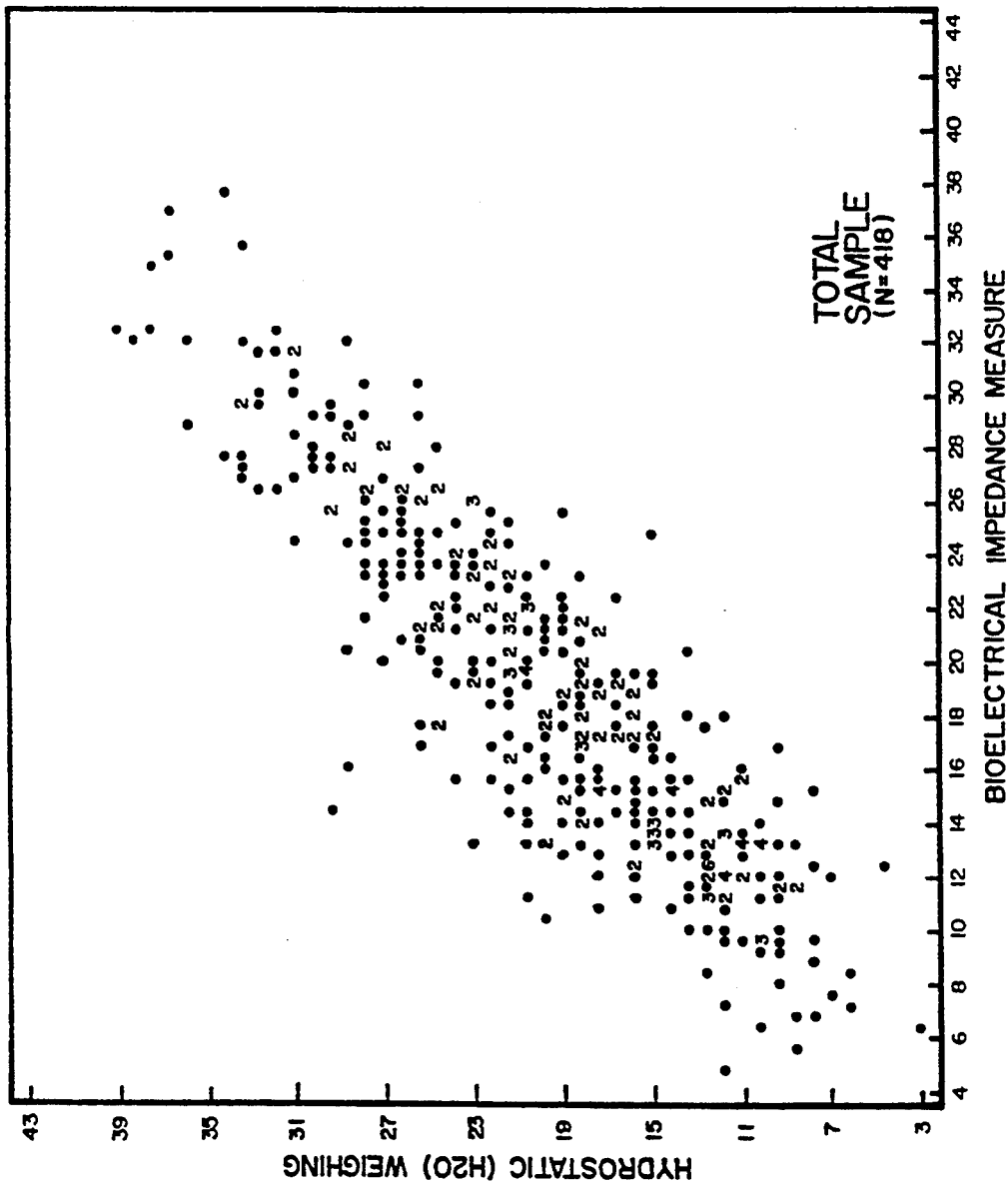
FIG. 12 is a graph which reflects the total sample referred to in Example I in accordance with the present invention.
Figure 13:
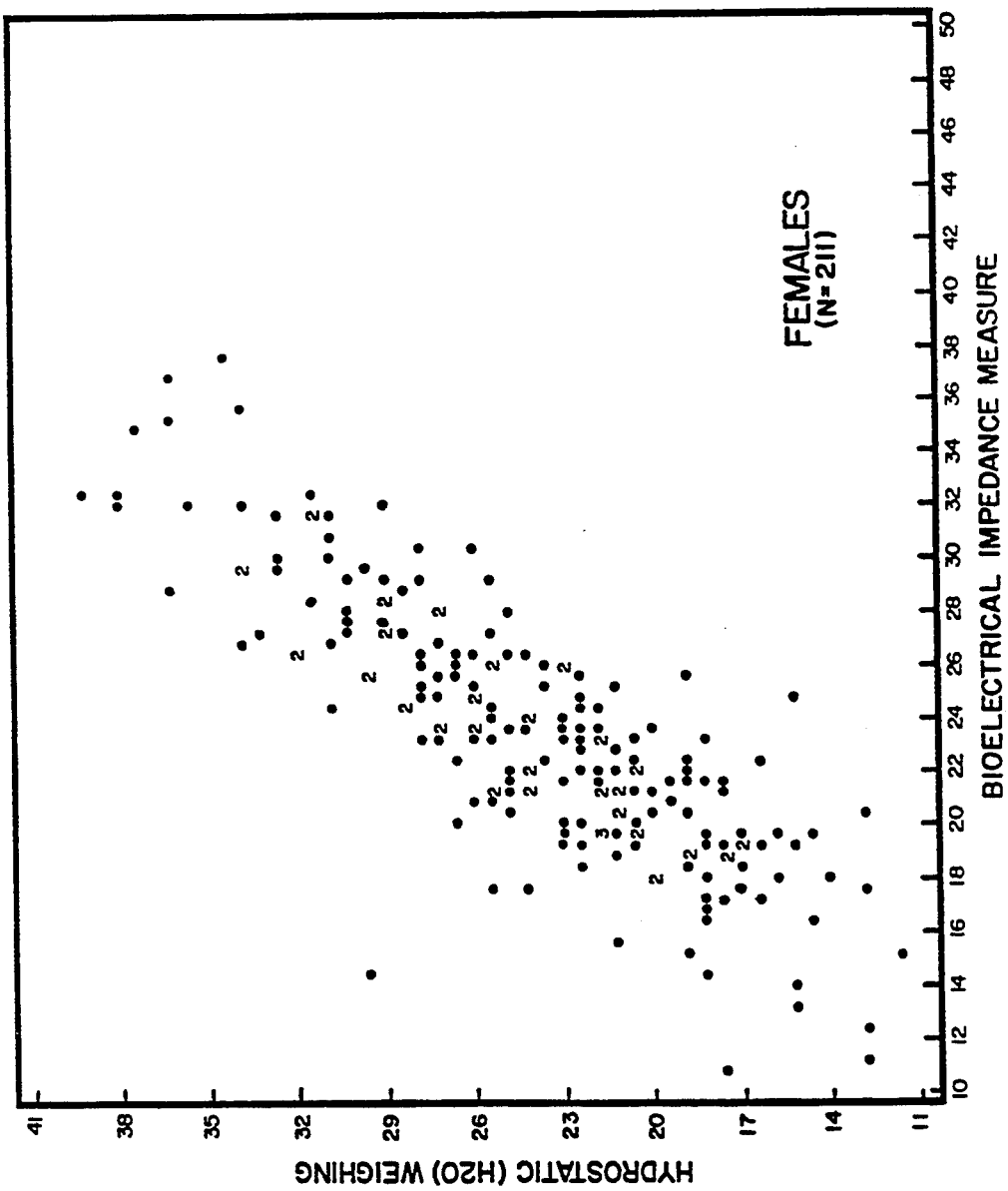
FIG. 13 is a graph which reflects the female component of the total sample referred to in Example I in accordance with the present invention.
Figure 14:
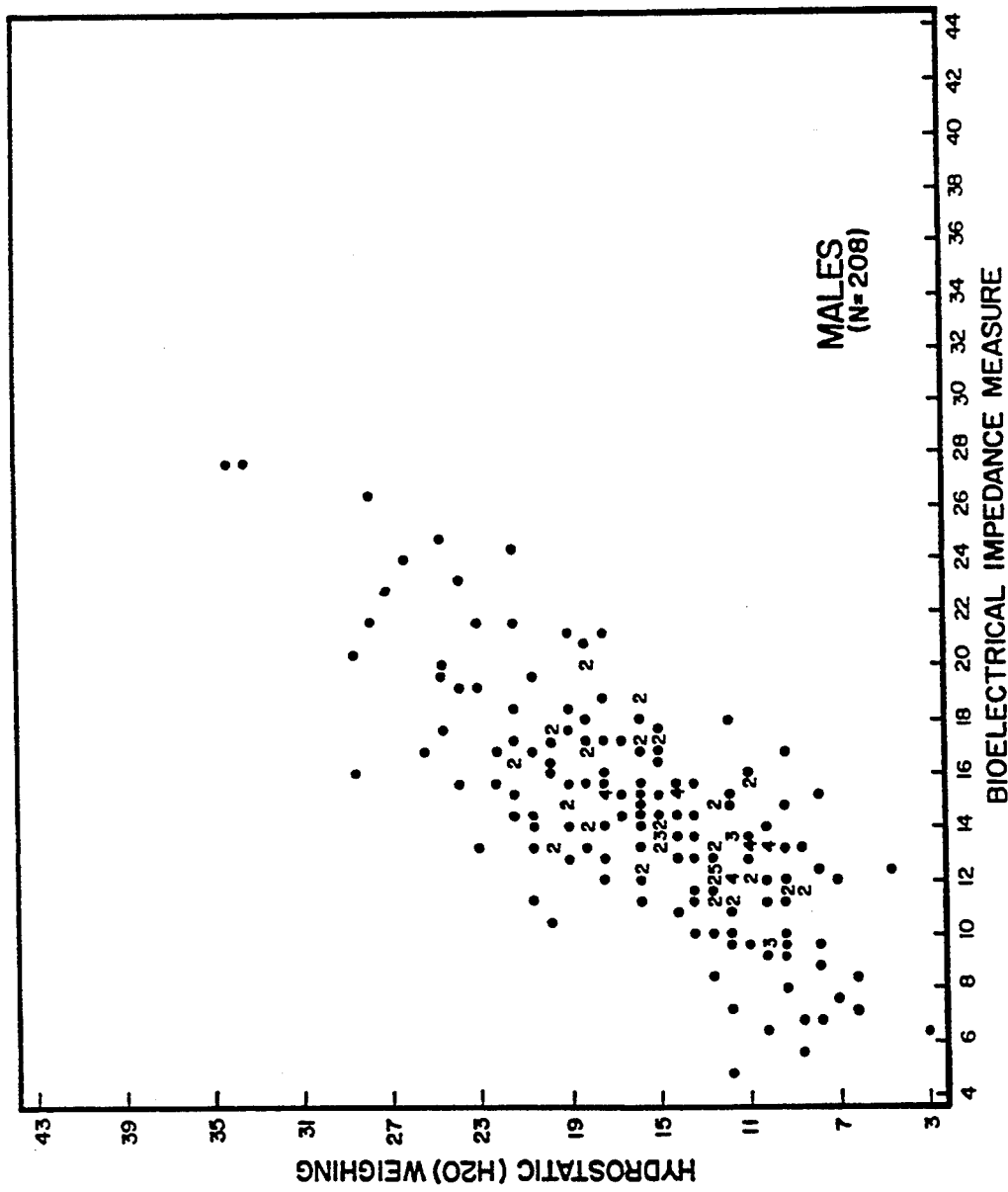
FIG. 14 is a graph which reflects the male component of the sample referred to in Example I in accordance with the present invention.
Figure 17:
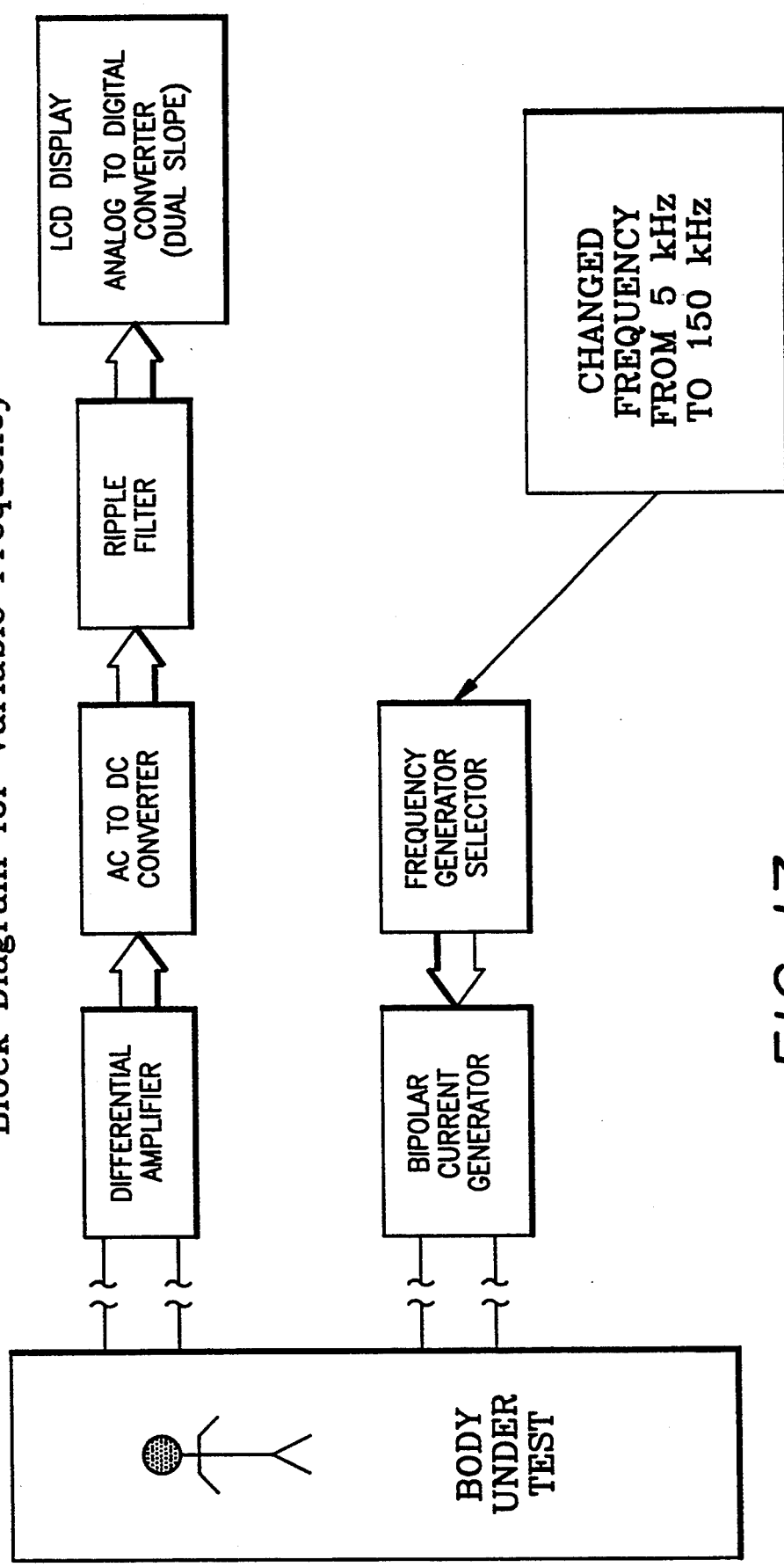
FIG. 17 is AnthroImpedance site measurements for males in accordance with the present invention.
Figure 18:
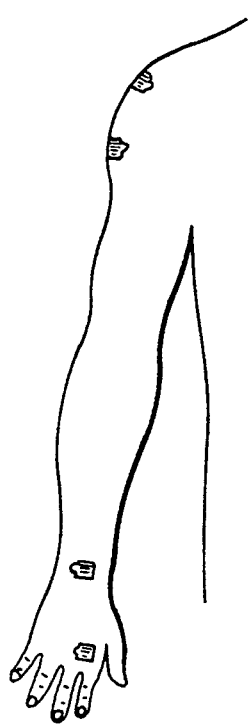
FIG. 18 is schematic of segmental site placement on an arm of a patent to be evaluated in accordance with one embodiment of the invention.
Figure 19:
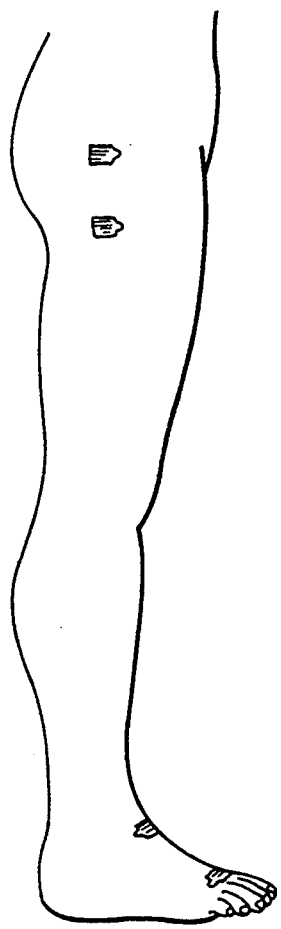
FIG. 19 is schematic of segmental site placement on a leg of a patent to be evaluated in accordance with one embodiment of the invention.
Figure 20:
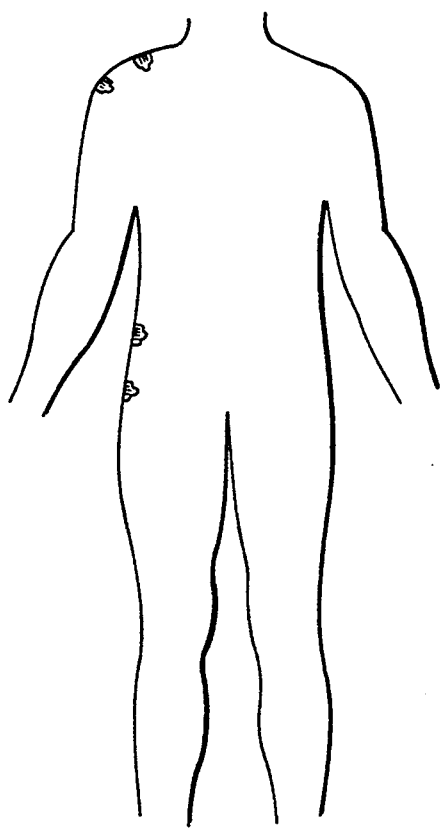
FIG. 20 is schematic of segmental site placement on a torso of a patent to be evaluated in accordance with one embodiment of the invention.
Figure 29:
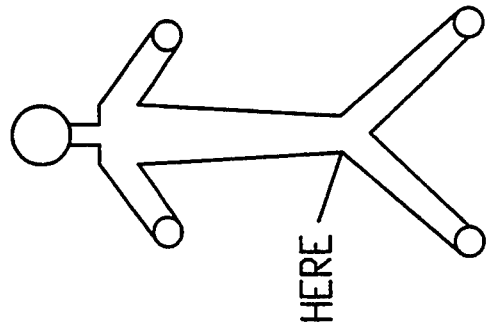
FIG. 29 is a depiction of an anthroimpedance input on a display screen in accordance with the present invention.

FIG. 8 represents one embodied individual progression through a population prediction formula.

a) Biological data input:
  1) Bio-impedance
  2) Age
  3) Height
  4) Weight
  5 Sex
b) Algorithm formula determination of body analysis formula constant based on body density and impedance:

e.g. If body density is (1.9 and impedance (400 then $X = 2.835$

Note: X is the body analysis formula constant.
  c) Population Prediction formula:

After phase one (a) and two (b) are complete, the main prediction formula which has been modified by the algorithm analyzes the data to predict body composition.

e.g. Percent fat $= (4.95/x - 4.5)$

Note: X is the constant from the algorithm.
  d) Then, insert percent fat into the sex specific formula outlined on page 30.

| | |
|---|---|
| | FEMALES |
| % FAT = | 0.457 X (IMPEDANCE % FAT) − 7.38 X (SHOULDER/ABDOMEN) + 0.181 X (RIGHT THIGH) X − 0.362 X (KG) + 0.500 X (GLUTEUS) + 0.236 X (ABDOMINAL 2) − 0.275 (HT) − 0.380 X (NECK) + 1.529 |
| | MALES |
| | ANTHRO-IMPEDANCE FORMULA |
| % FAT = | 0.773 X (IMPEDANCE % FAT) − 0.341 X (ARM LENGTH) + 0.303 X (SHOULDER/ABDOMEN) − 0.143 X (CHEST) − 4.974 X (THIGH/CALF) + 22.990 |

The inventive system preferably includes an attached microprocessor to perform the data processing tasks for body composition testing and analysis. The Computer desirable and has capacity for expandable features. (See FIG. 9)

Preferably the Computer is permanently mounted and cannot be removed from a transport case. A 6 volt adapter may be used to power the micro-processor.

INDICATOR MEANS FOR DISPLAYING DATA

Preferably a Printer such as a Color printer (324 CPS) is utilized in the system. A brief explanation for operation is provided herein.

TEST PROCEDURE

Height/Weight and Proper Patient Position (1) Record patient's height and weight. (Height in inches, weight in pounds.) Do not use data supplied by patient. Accurate height and weight measurements are essential for accurate results. Remove patient's shoes for both measurements. Also remove the sock/hose on the right foot. (The site for distal electrode sensor placement.)

(2) Position the patient prone on a non-conductive surfaced table. Do not test a patient lying on a tile or carpeted floor. Static electricity contained in these surfaces interferes with accuracy. The patient must be prone to minimize interference from muscle contractions. (Antagonist muscle contractions in standing or sitting patients create inaccurate Impedance results.)

(3) Arrange the patient's limbs so they are slightly apart, hands not touching the torso, feet not touching each other.

OPERATION CHECK LIST a) Attach Electrode Sensors to Patient Lead Cables.
b) Remove Patient's shoes and right sock/hose.
c) Measure Patient's height.
d) Weigh patient.
e) Record Patient Height and Weight on Patient Data Form.
f) Place Patient prone on table.
g) Palpate Electrode Sensor locations.
h) Place Electrode Sensors to right hand and right foot.
i) Collect Patient Impedance reading.
j) Record Impedance reading on Patient Data Form.
j-1) Collect and record said anthropometric measurements on form.
k) Select program on the Main Menu and ENTER.
l) ENTER information needed for Patient Data Input.
m) Remove Printout from the Printer.

ILLUSTRATIVE EXAMPLES

The following specific examples will be helpful to a clearer understanding of the unique features of the present invention:

Example I

A study was conducted to evaluate the validity of bio-electrical impedance as an accurate assessment of body composition. Two-hundred and forty nine male and female volunteers from the University of Southern California were used as subjects. Each subject reported to the Exercise Physiology lab at USC in a normally hydrated state. Body composition evaluation was made by hydrostatic weighing (H20) and bioelectrical impedance (Imp). Hydrostatic weighing was done in a seated position in a 1000 gallon tank using a Chatilion autopsy scale. A minimum of 5 trials was made on each subject. Residual lung volume was measured utilizing the oxygen dilution technique and employing a Hewlett-Packard Nitrogen analyzer. Body fat was calculated using the formula of Brozek, et al. ($4.57/$Density—$4.142 \times 100\%$). Bio-electrical impedance was measured on each subject employing the standard procedures for the technique. Average body fat for the males (N=117) was 14.1% measured by H20 and 14.3% as measured by Imp. The validity coefficient for this group was $r = -0.78$ and the standard error of estimate (SEE) was 3.07%. The corresponding values for the female group (N=132) were follows: Average body fat from H20=23.5%; from Imp=23.3%; validty coefficient, $r=0.80$; SEE=2.879%. The results of the present study support the use of the bio-electrical impedance technique as a method of assessing body composition in normal, healthy individuals. (See FIGS. 10 through 15)

Example II

A study was conducted to evaluate the validity of bio-electrical impedance as an accurate assessment of body composition. Four-hundred and eighteen male and female volunteers from the University of Southern California were used as subjects. Each subject reported to the Exercise Physiology lab at USC in a normally hydrated state. Body composition evaluation was made by hydrostatic weighing (H20) and bioelectrical impedance (Imp.) [BioAnalogics—"Consultant" System] Hydrostatic weighing was done in a seated position in a 1000 gallon tank using a Chatilon autopsy scale. A minimum of 5 trials was made on each subject. Residual lung volume was measured utilizing the oxygen dilution technique and employing a Hewlett-Packard Nitrogen analyzer. Body fat was calculated using the formula of Brozek et.al. ($4.57/$Density—$4.142 \times 100\%$). Bio-electrical impedance was measured on each subject in a supine position. Average body fat for the male (N=208) was 15.2% measured by H20 and 14.4% as measured by Imp. The range of body fat for this group was 3–35%. The validity coefficient for this group was $r=0.76$ and the standard error of estimate (SEE) was 3.34%. The corresponding values for the female group (N=211) were as follows: Average body fat from H20=23.9%; from Imp=23.4%; range=11–39%; validity coefficient, $r=0.83$; SEE=3.15%. The results of the present study support the use of the bio-electrical impedance technique as a method of assessing body composition in normal, healthy individuals.

Example III

This study was an attempt to further elucidate the use of bioelectrical impedance to predict body composition in a large and heterogenous population. Densitometry (H20) and bio-impedance (BI) were measured on 426 females and 343 males. Mean values for percent body fat were 23% for the females and 15% for the males and were essentially similar for the two methods. Employing a series of circumference measures taken on 425 females and 343 males, a prediction formula (BioAnalogics) incorporating impedance and anthropometry was utilized Validity coefficients improved to $R=0.86$ (females) and $R=0.85$ (males) while the standard errors were reduced to 3.08% and 2.97%, for the female and male groups respectively. This study confirms that the use of bio-impedance and specific circumference measurements can be combined to predict body composition accurately in subjects with a wide range of body composition.

EXAMPLE IV

University of Southern California sought to test the hypothesis that there was a characteristic alteration of body water distribution in Pregnancy Induced Hypertension (PIH) that was detectable by electrical bioimpedance. Fifteen ambulatory patients with PIH and 15 height (L) and gestational age matched controls at 37–42 weeks gestation had total body electrical bioimpedance determined using the Body Composition Analyzer (BioAnalogics, Inc., Los Angeles, Calif.). Segmental impedance of the upper and lower extremity was determined at the same time. The relationship between impedance (I) and the volume (V) of the conductor (water) is described by $V=L2/1$. The data summarized below (mean+1SEM):

|           | Normal (n = 15) |        | PIH (n = 15) |        | p    |
|-----------|-----------------|--------|--------------|--------|------|
| Total I   | 563             | (+46)  | 437          | (+50)  | .001 |
| Leg I     | 138             | (+13)  | 94           | (+20)  | .001 |
| Arm I     | 115             | (+17)  | 95           | (+11)  | .001 |
| Leg I/Arm I | 1.22          | (+.17) | 1.00         | (+.18) | .003 |

These results demonstrate that in patients with PIH there is a significant accumulation of upper and lower extremity water reflected by the lower I for these segments. There was a proportionally greater accumulation of water in the lower extremity over the upper extremity as reflected by the significantly lower ratio of LegI/ArmI in patients with PIH. Conclusion: The quantity and distribution of body water is significantly different in patients with PIH as detected by the BioAnalogics electrical bioimpedance system. This study confirmed that the use of Total Body and Segmental impedance can detect volume and distribution in TBW and allow for proactive medical treatment.

Accordingly, the unique system of the present invention provides an accurate valid measurement of human body composition consisting of fat tissue, lean tissue and body water. The inventive methodology provides a procedure for quantitative measurement of the conductive potential of the body, which is based on the lean tissue content of the body, in a convenient and reliable manner. Although a preferred embodiment of the invention has been shown and described, it will be apparent that other adaptation and modifications can be made without departing from the spirit and scope of the invention. Accordingly, the invention is not to be limited, except as by the following claims.

We claim:

1. A system for acquisition of body impedance data for quantitative measurement of conductive potential of the body, the system comprising in combination:
   a) a plurality of electrode sensors for mounting to a patient's body to be analyzed at prescribed locations forming a tetrapolar system;
   b) mounting means for removably attaching said electrode sensors to a Kelvin Bridge bio-impedance meter system having four terminal leads;
   c) means for generating a current flow through said electrode sensors at a frequency of from about 40 Kilohertz to about 60 Kilohertz, thereby producing a body impedance signal having an output range of from about 0 to 1,000 ohms;
   d) means for accepting input variables comprised of biological patient data including, height, weight, age and sex and bio-impedance signal derived from the means set forth in step (c) to determine a population specific variable and to produce a corresponding electrical signal;
   e) means for manipulating said electrical signals derived from said means for generating a current flow and said means for accepting input variables to produce a resultant output signal;
   f) indicator means for displaying said resultant output signal to provide quantitative measurement of conductive potential of said patient's body based on lean tissue content of said patient; and
   g) means for comparing said resultant output signal with a control signal to produce an output representation of fat tissue, lean tissue and body water; and
   h) second means for comparing the signal derived from step (g) with known anthropometric data to produce an output signal representative of fat, lean tissue and body water.
   i) an additional means for generating a current flow through said electrode sensors at frequencies ranging from about 5 KHZ to about 150 KHZ, thereby producing additional bioimpedance signals having an output range from about 0 to 10,000 ohms.
   j) means for modifying bioimpedance signals from (i) in such a way to predict Total Body Water, Extracellular Body Mass and Intracellular Body Cell Mass for different individuals or changes in the above TBW, ECM and BCM in the same individual over time.
   k) an additional means for removably mounting electrode sensors to the defined anatomical extremes of segments of the human body (e.g., leg, arm, torso) and means to generate and measure segmental impedance signals;
   l) an additional means for manipulating total body impedance, segmental impedance and ratios of the above in conjunction with multiple variable frequencies, in order to predict the quantity and distribution and changes in the quantity and distribution of Total Body Water, Extracellular Body Mass volume and Intracellular Body Cell Mass.

2. The system for body impedance data acquisition as defined in claim 1, wherein one of said electrode sensors is adapted to be mounted on the dorsal aspect of the patient's right hand.

3. The system for body impedance data acquisition as defined in claim 1, wherein one of said electrode sensors is adapted to be mounted at the distal end of the second metacarpal of the patient's right hand.

4. The system for body impedance data acquisition as defined in claim 1, wherein one of said electrode sensors is adapted to be mounted in between the medial and the lateral malleoli of the patient's right foot.

5. The system for body impedance data acquisition as defined in claim 1, wherein one of said electrode sensors is adapted to be mounted at the distal portion of the first metatarsal of the patient's right foot.

6. The system for body impedance data acquisition as defined in claim 1, wherein said means for generating a current flow operates at a frequency of about 50 Kilohertz.

7. The system for body impedance data acquisition as defined in claim 1, and further comprising a power supply for the system.

8. The system for body impedance acquisition as defined in claim 1, wherein said means for generating a variable current operates between about 5 KHZ to 150 KHZ.

9. The system for segmental impedance as defined in claim 1, wherein the said electrode sensors are mounted at the anatomical extremes of the segment to be measured (e.g., the arm, the leg, the torso).

* * * * *